US008703719B1

(12) United States Patent
Abraham et al.

(10) Patent No.: US 8,703,719 B1
(45) Date of Patent: Apr. 22, 2014

(54) METHOD AND COMPOSITION FOR IMPROVED MUSCLE PERFORMANCE

(75) Inventors: Sal Abraham, Boca Raton, FL (US); Chris Ferguson, Boca Raton, FL (US)

(73) Assignee: Bio-Engineered Supplements and Nutrition, Inc., Evanston, IL (US)

( * ) Notice: Subject to any disclaimer, the term of this patent is extended or adjusted under 35 U.S.C. 154(b) by 301 days.

(21) Appl. No.: 12/782,702

(22) Filed: May 18, 2010

Related U.S. Application Data

(60) Provisional application No. 61/179,272, filed on May 18, 2009.

(51) Int. Cl.
*A01N 43/04* (2006.01)
(52) U.S. Cl.
USPC .............................................. 514/23; 424/439
(58) Field of Classification Search
USPC .......................... 424/425; 426/62; 514/12, 23
See application file for complete search history.

(56) References Cited

U.S. PATENT DOCUMENTS

| | | | |
|---|---|---|---|
| 5,550,113 | A | 8/1996 | Mann |
| 5,719,119 | A | 2/1998 | Veech |
| 5,968,544 | A | 10/1999 | Howard et al. |
| 5,968,900 | A | 10/1999 | Greenhaff et al. |
| 6,093,697 | A | 7/2000 | Larner et al. |
| 6,100,287 | A | 8/2000 | Stevens et al. |
| 6,136,339 | A | 10/2000 | Gardiner |
| 6,274,161 | B1 | 8/2001 | Howard et al. |
| 6,326,513 | B1 | 12/2001 | An et al. |
| 6,488,955 | B1 | 12/2002 | Decombaz et al. |
| 6,620,425 | B1 | 9/2003 | Gardiner |
| 7,329,763 | B1 | 2/2008 | Molino |
| 7,465,812 | B2 | 12/2008 | Molino |
| 7,479,560 | B2 | 1/2009 | Molino |
| 7,482,474 | B2 | 1/2009 | Molino |
| 2002/0018818 | A1* | 2/2002 | Suzuki et al. ................. 424/725 |
| 2004/0219141 | A1 | 11/2004 | Kashimura et al. |
| 2006/0096587 | A1 | 5/2006 | Brouns et al. |
| 2008/0044541 | A1 | 2/2008 | Rathjen et al. |
| 2008/0269117 | A1* | 10/2008 | Hageman ........................ 514/12 |
| 2009/0162483 | A1* | 6/2009 | Constantine et al. ........... 426/62 |
| 2009/0181903 | A1* | 7/2009 | Wolfe et al. ..................... 514/23 |
| 2009/0281055 | A1 | 11/2009 | Kneller |

OTHER PUBLICATIONS

Rehder, D. et al., Insulin-Mimetic Oxovanadium-Picolinates, Abstracts 12th International Conference on Biological Inorganic Chemistry, 2005, http://www.umich.edu/~icbic/Abstracts/371775-1.pdf.
Ren, J.M. et al., Effects of Beta-Guanidinopropionic Acid-Feeding on the Patterns of Myosin Isoforms in Rat Fast-Twitch Muscle. Pflugers Arch. Jul. 1995;430(3):389-393, Abstract Only.
Reul, B.A. et al., Effects of Vanadium Complexes with Organic Ligands on Glucose Metabolism: A Comparison Study in Diabetic Rats. Br J Pharmacol. Jan. 1999;126(2):467-477.
Roberfroid, M. Dietary Fiber, Inulin, and Oligofructose: A Review Comparing their Physiological Effects, Crit. Rev. Food Sci. Nutri., 1993, vol. 33, No. 2, 103-148, Abstract Only.
Roberfroid, M.B. Introducing Inulin-Type Fructans. Br J Nutr. Apr. 2005;93 Suppl1:S13-S25.
Roffey, B. et al., Cinnamon Water Extracts Increase Glucose Uptake but Inhibit Adiponectin Secretion in 3T3-L1 Adipose Cells. Mol Nutr Food Res. Aug. 2006;50(8):739-745, Abstract Only.
Rowlands, D.S. et al., Glucose Polymer Molecular Weight Does not Affect Exogenous Carbohydrate Oxidation, Med. Sci. Sports Exercise, 2005, vol. 37, No. 9, 1510-1516.
Roy, B.D. et al., Acute Plasma Volume Expansion Alters Cardiovascular but Not Thermal Function During Moderate Intensity Prolonged Exercise. Can J Physiol Pharmacol. Mar. 2000;78(3):244-250, Abstract Only.
Roy, B.D. et al., Substrate Turnover and Oxidation During Moderate-Intensity Exercise Following Acute Plasma Volume Expansion. Horm Metab Res. Feb. 2000;34(2):93-101, Abstract Only.
Sands, A.L. et al., Consumption of the Slow-Digesting Waxy Maize Starch Leads to Blunted Plasma Glucose and Insulin Response but Does Not Influence Energy Expenditure or Appetite in Humans, Nutrition Research, 2009, vol. 29, 383-390.
Sapata, K.B. et al., Effect of Prior Consumption of Carbohydrate on the Glycaemia and Performance, Revista Brasileira de Medicina do Esporte, Jul./Aug. 2006, vol. 12, Issue 4.
Sato, K. et al., Dietary Palatinose and Oleic Acid Ameliorate Disorders of Glucose and Lipid Metabolism in Zucker Fatty Rats. J Nutr. Aug. 2007;137(8):1908-1915, Abstract Only.
Schoch, R.D. et al., The Regulation and Expression of the Creatine Transporter: A Brief Review of Creatine Supplementation in Humans and Animals. J Int Soc Sports Nutr. 3(1):60-66, 2006.
Schwab, U. et al., Betaine Supplementation Decreases Plasma Homocysteine Concentrations but Does Not Affect Body Weight, Body Composition, or Resting Energy Expenditure in Human Subjects. Am J Clin Nutr. Nov. 2002;76(5):961-967.
Schwab, U. et al., Orally Administered Betaine has an Acute and Dose-Dependent Effect on Serum Betaine and Plasma Homocysteine Concentrations in Healthy Humans. J Nutr. Jan. 2006;136(1):34-38.
Seidman, D.S. et al., The Effects of Glucose Polymer Beverage Ingestion During Prolonged Outdoor Exercise in the Heat. Med Sci Sports Exerc. Apr. 1991;23(4):458-462, Abstract Only.
Shechter, Y. Insulin-Mimetic Effects of Vanadate. Possible Implications for Future Treatment of Diabetes, Diabetes, 1990, 1-5, vol. 39, Issue 1, http://diabetes,diabetesjournals.org/content/39/1/1.abstract.
Sparks, et al., Pre-Exercise Carbohydrate Ingestion: Effect of the Glycemic Index on Endurance Exercise Performance, Med. Sci. Sports Exercise, 1998, 844-849, vol. 30, Issue 6.
Srivastava, A.K. et al., Insulin-Mimetic and Anti-Diabetic Effects of Vanadium Compounds. Diabet Med. Jan. 2005;22(1):2-13, Abstract Only.
Stephens, F.B. et al., Post-Exercise Ingestion of a Unique, High Molecular Weight Glucose Polymer Solution Improves Performance During a Subsequent Bout of Cycling Exercise. J Sports Sci. Jan. 15, 2005;26(2):149-154; 2007, p. 1-6 (iFirst).

(Continued)

*Primary Examiner* — Walter Webb
(74) *Attorney, Agent, or Firm* — Amin Talati, LLC; Janine A. Moderson; George M. Carrera, Jr.

(57) ABSTRACT

A method for regulating glucose release, promoting glycogen conservation, and/or glycogen synthesis includes orally administering an effective amount of a nutritional composition comprising fast and slow absorbing carbohydrates in combination with an insulinomimetic compound to provide a steady release of glucose from the gastrointestinal tract.

20 Claims, 5 Drawing Sheets

(56) References Cited

OTHER PUBLICATIONS

Stewart, I. et al., Phosphate Loading and Effects on VO2 Max in Trained Cyclists. Res Q Exerc Sport. Mar. 1990;61(1):80-84, Abstract Only.

Stout, J.R. et al., Effects of Twenty-Eight Days of Beta-Alanine and Creatine Monohydrate Supplementation on the Physical Working Capacity at Neuromuscluar Fatigue Threshold. J Stength Cond Res. Nov. 2006; 20(4):928-931, Abstract Only.

Strowski, M.Z. et al. Small-Molecule Insulin Mimetic Reduces Hyperglycemia and Obesity in a Non-Genetic Mouse Model of Type 2 Diabetes, Endocrinology, 2004, 5259-68, vol. 145.

Sugawara, J. et al., Effects of Nitric Oxide Synthase Inhibitor on Decrease in Peripheral Arterial Stiffness with Acute Low-Intensity Aerobic Exercise. Am J Physiol Heart Circ Physiol. Dec. 2004;287(6):H2666-H2669.

Sugiura, K. et al., Effect of Carbohydrate Ingestion on Sprint Performance Following Continuous and Intermittent Exercise. Med Sci Sports Exerc. Nov. 1998;30(11):1624-1630.

Suzuki, Y. et al. Anitobesity Activity of Extracts from *Lagerstroemia speciosa* L. Leaves on Female KK-Ay Mice. J Nutr Sci Vitaminol (Tokyo). Dec. 1999;45(6):791-795, Abstract Only.

Takeda, E. et al., Control of Oxidative Stress and Metabolic Homeostasis by the Suppression of Postprandial Hyperglycemia. J Med Invest. Nov. 2005;52(S)259-265.

Talmadge, R.J. et al., Glucose Uptake and Glycogen Synthesis in Normal and Chronically Active Muscles, Am J. Physiol., 1993, vol. 264, No. 3, E328-E333.

Tarini, J. Does Inulin Reduce Postprandial Free Fatty Acid Rebound?, Graduate Department of Nutritional Sciences, University of Toronto, 2009.

Tarini, J. et al., The Fermentable Fibre Inulin Increases Postprandial Serum Short-Chain Fatty Acids and Reduces Free-Fatty Acids and Ghrelin in Healthy Subjects, Appl Physiol Nutr Metab. Feb. 2010;35(1):9-16, Abstract Only.

Thompson, K. H. Vanadium and Diabetes. Biofactors. 1999;10(1):43-51, Abstract Only.

Tipton, K.D. et al. Timing of Amino Acid-Carbohydrate Ingestion Alters Anabolic Response of Muscle to Resistance Exercise. Am J Physiol Endocrinol Metab. Aug. 2001;281(2):E197-E206.

Tsintzas, K. et al., Human Muscle Glycogen Metabolism During Exercise. Effect of Carbohydrate Supplementation. Sports Med. Jan. 1998;25(1):7-23, Abstract Only.

Tungland, B. Inulin Offers Strong Base for Sugar Replacement, Organic Processing Magazine, Apr. 2010, http://www.organicprocessing.com/opjs06/opjs06ingredients.htm.

Van Amelsvoort, J.M. et al., Amylose-Amylopectin Ratio in a Meal Affects Postprandial Variables in Male Volunteers. Am. J. Clinical Nutrition, 1992, 712-718, vol. 55.

Vanschoonbeek, K. et al., Slowly Digestible Carbohydrate Sources Can be Used to Attenuate the Postprandial Glycemic Response to the Ingestion of Diabetes-Specific Enteral Formulas, Diabetes Educator, 2009, 631-40, vol. 35.

Von Restorff, W. et al., Effect of Increased Blood Fluidity Through Hemodilution on Coronary Circulation at Rest and During Exercise in Dogs. Pflugers Arch. 1975;357(1-2):15-24.

Wallis, G.A. et al., Oxidation of Combined Ingestion of Maltodextrins and Fructose During Exercise, Med. Sci. Sports Exercise, 2005, vol. 37, No. 3, 426-432.

Weatherwax, P.A. A Rare Carbohydrate in Waxy Maize. Genetics. Nov. 1922;7(6):568-572.

Webb, A. et al., Acute Blood Pressure Lowering, Vasoprotective, Antiplatelet Properties of Dietary Nitrate Via Bioconversion to Nitrate. Hypertension. Mar. 2008;51(3):784-790, Abstract Only.

Williams, C.M. Effects of Inulin on Lipid Parameters in Humans, J. Nutrition, 1999, 1471S-1473S, vol. 129.

Wyss, M. et al., Creatine and Creatinine Metabolism. Physiol Rev. Jul. 2000;80(3):1107-1213.

Yamada, K. et al., Effect of Corosolic Acid on Gluconeogenesis in Rat Liver. Diabetes Res Clin Pract. Jan. 2008; 80(1):48-55, Abstract Only.

Yeung, N.H. Insulin-Mimetic Vanadium IV/V Complexes, Inorganic Literature Seminar, Oct. 21, 2004, accessed at http://chemistry.illinois.edu/research/inorganic/seminar_abstracts/2004-2005-Yeung.Abstract.LitSeminar.pdf.

Ziegenfuss, T. et al., Effects of a Water-Soluble Cinnamon Extract on Body Composition and Features of the Metabolic Syndrome in Pre-Diabetic Men and Women. J. Int. Soc. of Sports Nutrition. 3(2): 45-53, 2006.

Zoeller, R.F. et al., Effects of 28 Days of Beta-Alanine and Creatine Monohydrate Supplementation on Aerobic Power, Ventilatory and Lactate Thresholds, and Time to Exhaustion. Amino Acids. Sep. 2007;33(3):505-510, Abstract Only.

Zorbas, Y.G. et al., Phosphate Loading Test Influences on Endurance-Trained Volunteers During Restriction of Muscular Activity and Chronic Hyperhydration. Biol Trace Elem Res. Apr. 1995;48(1):51-65, Abstract Only.

Parkinson, T.M. Hypolipidemic Effect of Orally Administered Dextran and Cellulose Anion Exchangers in Cockerels and Dogs. J Lipid Res. Jan. 1967;8(1):24-29.

Parkinson, T.M. Metabolism of Orally Administered Dextran and Sephadex Derivatives in Rats. Nature. Jul. 1967;215(5099):415-416, Abstract Only.

Phillips, S.M. et al., Effect of Acute Plasma Volume Expansion on Substrate Turnover During Prolonged Low Intensity Exercise. Am J Physiol. Aug. 1997;273(2):297-304, Abstract Only.

Piehl, A.K. et al., Muscle Glycogen Resynthesis Rate in Humans After Supplementation of Drinks Containing Carbohydrates with Low and High Molecular Masses. Eur J Appl Physiol. Mar. 2000;81(4):346-351, Abstract Only.

Qin, B. et al., Cinnamon Extract Prevents the Insulin Resistance Induced by a High-Fructose Diet. Horm Metab Res. Feb. 2004;36(2):119-125, Abstract Only.

Rankin, J.W. Glycemic Index and Exercise Metabolism, Gatorade Sports Science Institute, Sports Science Exchange, SSE#64, vol. 10(No. 1), 1997, http://www.ultrunr.com/glycemic.html.

Rasio, E.A. et al., Diffusion of Glucose, Insulin, Inulin, and Evans Blue Protein into Thoracic Duct Lymph of Man, J. Clinical Investigation, 1967, 903-12, vol. 46, Issue 6.

Rasmussen, B.B. et al., An Oral Essential Amino Acid-Carbohydrate Supplement Enhances Muscle Protein Anabolism After Resistance Exercise. J Appl Physiol. Feb. 2000;88(2):386-392.

Ball, T.C. et al. Periodic Carbohydrate Replacement During 50 min of High-Intensity Cycling Improves Subsequent Sprint Performance. Int J Sport Nutr. Jun. 1995;5(2):151-158.

Coyle, E.F. et al. Maximal oxygen uptake relative to plasma volume expansion. Int J Sports Med., Apr. 1990;11(2):116-119, Abstract Only.

Green, H.J. et al. Reduced muscle lactate during prolonged exercise following induced plasma volume expansion. Can J Physiol Pharmacol. Dec. 1997;75(12):1280-1286, Abstract Only.

Hardin, D.S. et al., Mechanisms of Enhanced Insulin Sensitivity in Endurance-Trained Athletes: Effects of Blood Flow and Differential Expression of GLUT4 in Skeletal Muscles, J. Clinical Endocrinology & Metabolism, 1995, vol. 80, 2437-2446, Abstract Only.

He, J. et al., Slowly Digestible Waxy Maize Starch Prepared by Octenyl Succinic Anhydride Esterifcation and Heat—Moisture Treatment: Glycemic Response and Mechanism. Biomacromolecules, 2008, 9 175-184.

Helyar, R. et al., Comparitive effects of acute volume expansion and short-term training on thermal and cardiovascular responses to prolonged exercises. Can J Physiol Pharmacol. Sep. 1996;74(9):1087-1094, Abstract Only.

Johannsen, N.M. et al. Effect of Preexercise Ingestion of Modified Cornstarch on Substrate Oxidation During Endurance Exercise. Int J Sport Nutr Exerc Metab. Jun. 2007;17(3):232-243.

Jozsi, A.C. et al. The Influence of Starch Structure on Glycogen Resynthesis and Subsequent Cycling Performance. Int J Sports Med. Jul. 1996;17(5):373-378.

Roy, B.D. et al. Acute plasma volume expansion in the untrained alters the hormonal response to prolonged moderate-intensity exercise. Horm Metab Res. Apr. 2001;33(4):238-245, Abstract Only.

(56) References Cited

OTHER PUBLICATIONS

Tsuji, Y. et al., Digestion and Absorption of Sugars and Sugar Substitutes in Rat Small Intestine, J. Nutritional Science & Vitaminology (Tokyo), 1986, 93-100, Abstract Only.

Abrams, S.A. et al., A Combination of Prebiotic Short- and Long-Chain Inulin-Type Fructans Enhances Calcium Absorption and Bone Mineralization in Young Adolescents. Am J Clin Nutr. Aug. 2005;82(2):471-476.

Achten, Juul et al., Exogenous Oxidation of Isomaltulose is Lower than That of Sucrose During Exercise in Men, J. Nutrition, 2007, 1143-48, vol. 137.

Anderson, G.H. et al., Inverse Association Between the Effect of Carbohydrates on Blood Glucose and Subsequent Short-Term Food Intake in Young Men, Am. J. Clinical Nutrition, 2002 vol. 76, 1023-1030.

Anderson, M.J. et al., Effect of Glycerol-Induced Hyperhydration on Thermoregulation and Metabolism During Exercise in Heat. Int J Sport Nutr Exerc Metab. Sep. 2001;11(3):315-333, Abstract Only.

Arai, H. et al., Effects of Palatinose-Based Liquid Diet (Inslow) on Glycemic Control and the Second Meal Effect in Healthy Men. Metabolism. Jan. 2007;56(1):115-121, Abstract Only.

Atkinson, W. et al., Dietary and Supplementary Betaine: Acute Effects on Plasma Betaine and Homocysteine Concentrations Under Standard and Postmethionine Load Conditions in Healthy Male Subjects. Am J Clin Nutr. Mar. 2008;87(3):577-585, Abstract Only.

Badmaev, V. et al., Vanadium: A Review in its Potential Role to Fight Diabetes. J Altern Complement. Med Jun. 1999;5(3):273-291, Abstract Only.

Behall, K.M. et al., Apparent Mineral Retention is Similar in Control and Hyperinsulinemic Men After Consumption of Highly Amylose Corn Starch. J Nutr. Jul. 2002;132(7):1886-91.

Behall, K.M. et al., Diets Containing Highly Amylose Versus Amlyopectin Starch: Effects on Metabolic Variables in Human Subjects. Am J Clin Nutr. Feb. 1989;49(2):337-44.

Behall, K.M. et al., Effect of Long Term Consumption of Amylose Vs Amlyopectin Starch on Metabolic Variables in Human Subjects. Am J Clin Nutr. Feb. 1995;61(2):334-40.

Behall, K.M. et al., Effect of Starch Structure on Glucose and Insulin Responses in Adults. Am J Clin Nutr. 1988;47:428-432.

Beliaeva, N.F. et al., Vanadium Compounds—A New Class of Therapeutic Agents for the Treatment of Diabetes Mellitus. Vopr Med Khim. Jul. 2000;46(4):344-60, English Abstract Only.

Beylot, M., Effects of Inulin-Type Fructans on Lipid Metabolism in Man and in Animal Models, British J. Nutrition. 2005, S163-S168, vol. 93, Suppl. 1.

Bird, S.P. et al., Effects of Liquid Carbohydrate/Essential Amino Acid Ingestion on Acute Hormonal Response During a Single Bout of Resistance Exercise in Untrained Men. Nutrition. Apr. 2006;22(4):367-375; Abstract Only.

Bird, S.P. et al., Independent and Combined Effects of Liquid Carbohydrates/Essential Amino Acid Ingestion on Hormonal and Muscular Adaptations Following Resistance Training in Untrained Men. Eur J Appl Physiol. May 2006;97(2):225-238, Abstract Only.

Bird, S.P. et al., Liquid Carbohydrate/Essential Amino Acid Ingestion During a Short Term Bout of Resistance Exercise Suppresses Myofibrillar Protein Degradation. Metabolism. May 2006;55(5):570-577, Abstract Only.

Bloom, W. et al., Dextran as a Source of Liver Glycogen and Blood Reducing Substance. Proc Soc Exp Biol Med. Nov. 1952; 81(2):501-503.

Bredle, D.L. et al., Phosphate Supplementation, Cardiovascular Function and Exercise Performance in Humans. J Appl Physiol. Oct. 1988;65(4):1821-1826, Abstract Only.

Brouns, F. et al., Effect of Carbohydrate Intake During Warming-Up of the Regulation of Blood Glucose During Exercise, Int. J. Sports Medicine, May 1989, vol. 10, Suppl. 1, S68-75.

Bryan, N.S. et al., Dietary Nitrite Supplementation Protects Against Myocardial Ischemia-Reperfusion Injury. Proc Natl Acad Sci Acad USA. Nov. 2007;104(48):19144-19149.

Burgess, M.L. et al., RPE, Blood Glucose, and Carbohydrate Oxidation During Exercise: Effects of Glucose Feedings, Med. Sci. Sports Exercise, 1991, 353-359, vol. 23, Issue 3.

Burke, L.M. et al., Muscle Glycogen Storage After Prolonged Exercise: Effect of the Frequency of Carbohydrate Feedings. Am J Clin Nutr. Jul. 1996;64(1):115-119.

Burke, L.M. et al., Muscle Glycogen Storage After Prolonged Exercise: Effect of the Glycemic Index of Carbohydrate Feedings. J App Physiol. Aug. 1993;75(2):1019-1023.

Cam, M.C. et al., Mechanisms of Vanadium Action: Insulin-Mimetic or Insulin-Enhancing Agent?, Can. J. Physiology Pharmacology, 2000, vol. 78(10), 829-847, Abstract Only.

Cao, H. et al., Cinnamon Extract and Polyphenols Affect the Expression of Tristetrapolin, Insulin Receptor and Glucose Transporter 4 Mouse 3T3-L1 Adipocytes. Arch Biochem Biophys. Mar. 2007;459(2):212-222, Abstract Only.

Claessens, M. et al., The Effect of Different Protein Hydrolysate/Carbohydrate Mixtures on Postprandial Glucagon and Insulin Responses in Healthy Subjects, European J. Clinical Nutrition, 2009, 48-56, vol. 63.

Coudray, C. et al., Effect of Insulin-Type Fructans of Different Chain Length and Type of Branching on Intestinal Absorption and Balance of Calcium and Magnesium in Rats, European J. Nutrition, 2003, 91-98, vol. 42.

Coussement, P.A.A., Inulin and Oligofructose: Safe Intakes and Legal Status, J. Nutr. Jul. 1999;129(7 Suppl): 1412S-1417S.

Currell, K. et al., Superior Endurance Performance with Ingestion of Multiple Transportable Carbohydrates, Med. Sci. Sports Exercise, 2008, 275-281, vol. 40, Issue 2.

Davenport, H.W. et al., The Metabolism of Creatine: the Role of Glycocyamine in Creatine Synthesis. Biochem J. Feb. 1938;32(2):262-270.

De Bock, K. et al., Fiber Type-Specific Muscle Glycogen Sparing Due Carbohydrate Intake Before and During Exercise. J Appl Physiol. Jan. 2007;102(1):183-188.

DeMarco, et al., Pre-Exercise Carbohydrate Meals: Application of Glycemic Index, Med. Sci. Sports Exercise, 1999, 164-170, vol. 31, Issue 1.

Derave, W. et al., Plasma Guanidino Compounds are Altered by Oral Creatine Supplementation in Healthy Humans. J Appl Physiol. Sep. 2004;97(3):852-857.

Derave, W. et al., Beta-Alanine Supplementation Augments Muscle Carnosine Content and Attenuates Fatigue During Repeated Isokinetic Contraction Bouts in Trained Sprinters. J Appl Physiol. Nov. 2007;103(5):1736-43, Abstract Only.

Dicter, N. et al., Alpha-Lipoic Acid Inhibits Glycogen Synthesis in Rat Soleus Muscle via its Oxidative Activity and the Uncoupling of Mitochondria, J. Nutrition, 2002, 3001-06, vol. 132.

Doyle, J.A. et al., Glycemic Response to Liquid, Solid and Gel Forms of Carbohydrate 718, Med. & Sci. in Sports & Exercise, 1997, 125, vol. 29(5), Meeting Abstract Only.

Dreyer, H.C. et al., Leucine-Enriched Essential Amino Acid and Carbohydrate Ingestion Following Resistance Exercise Enhances mTOR Signaling and Protein Synthesis in Human Muscle. Am J Physiol Endocrinol Metab. Feb. 2008;294(2):E392-E400, Abstract Only.

Ebeling, P. et al., Mechanism of Enhanced Insulin Sensitivity in Athletes: Increased Blood Flow, Muscle Glucose Transport Protein (GLUT-4) Concentration, and Glycogen Synthase Activity, J. Clin. Invest., Oct. 1993, vol. 92, 1623-1631.

Edes, T.E. et al., Glycemic Index and Insulin Response to a Liquid Nutritional Formula Compared with a Standard Meal, J. Am. College Nutrition, 1998, 30-35, vol. 17, Issue 1.

European Commission, Health & Consumer Protection Directorate General, Scientific Committee on Food, Opinion of the Scientific Committee on Food on a Dextran Preparation, Produced using *Leconostoc mesenteroides, Saccharomyces cerevisiae* and *Lactobacillus* Spp, As a Novel Food Ingredient in Bakery Products, expressed on Oct. 18, 2000, (European Commission, Brussels, Belgium).

Fielding, R.A. et al., Effect of Carbohydrate Feeding Frequencies and Dosage on Muscle Glycogen Use During Exercise, Med. Sci. Sports Exercise, 1985, vol. 17, No. 4, 472-476.

(56) References Cited

OTHER PUBLICATIONS

Foster-Powell, K. et al., International Table of Glycemic Index and Glycemic Load Values: 2002, Am. J. Clinical Nutrition, 2002, 5-56, vol. 76.

Freund, B.J. et al., Glycerol Hyperhydration: Hormonal, Renal, and Vascular Fluid Responses, J Appl Physiol. Dec. 1995;79(6):2069-2077, Abstract Only.

Fujiwara, T. et al., Effects of a Novel Palatinose Based Enteral Formula (MHN-01) Carbohydrate-Adjusted Fluid Diet in Improving the Metabolism of Carbohydrates and Lipids in Patients of Esophageal Cancer Complicated by Diabetes Mellitus. J Surg Res. Apr. 2007;138(2):231-240, Abstract Only.

Garcia-Vincente, S. et al., Oral Insulin-Mimetic Compounds that Act Independently of Insulin, Diabetes, 2007, 486-93, vol. 56(2), Abstract Only.

Gay-Crosier, F. et al., Anaphylaxis from Inulin in Vegetables and Processed Food. NEJM. May 2000;342(18):1372.

Goddard, M.S. et al., The Effect of Amylose Content on Insulin and Glucose Responses to Ingested Rice. Am J Clin Nutr. Mar. 1984;39(3):388-392.

Goforth, H.W. et al., Effects of Depletion Exercise and Light Training on Muscle Glycogen Supercompensation in Men. Am J Physiol Endocrinol Metab. Dec. 2003;285(6):E1304-E1311.

Green, D.J. et al., Comparison of Resistance and Conduit Vessel Nitric Oxide-Mediated Vascular Function in Vivo: Effects of Exercise Training. J Appl Physiol. Aug. 2004;97(2):749-755.

Guerrero-Ontiveros, M.L. et al., Creatine Supplementation in Health and Disease. Effects of Chronic Creatine Ingestion in Vivo: Down-Regulation of the Expression of Creatine Transporter Isoforms in Skeletal Muscle. Mol Cell Biochem. 1988;184:427-437, Abstract Only.

Harris, R.C. et al., Effect of Combined Beta-Alanine and Creatine Monohydrate Supplementation on Exercise Performance. Med Sci Sports Exerc. May 2003;35(5):S218.

Harris, R.C. et al., The Absorption of Orally Supplied Beta-Alanine and its Effect on Muscle Carnosine Synthesis in Human Vastus Lateralis. Amino Acids. May 2006;30(3):279-289.

He, J. et al., Slowly Digestible Waxy Maize Starch Prepared by Octenyl Succinic Anhydride Esterfication and Heat-Moisture Treatment: Glycemic Response and Mechanisms, Biomacromolecules, 2008, vol. 9, 175-184.

Heijnen, M.L. et al., Interaction Between Physical Structure and Amylose: Amylopectin Ratio of Foods on Postprandial Glucose and Insulin Responses in Healthy Subjects, Eur. J. Clinical Nutr., 1995, 49(6):446-457, Abstract Only.

Helyar, R. et al., Blood Metabolite and Catecholamine Responses to Prolonged Exercise Following Either Acute Plasma Volume Expansion or Short-Term Training. Eur J Appl Physiol. 1997;75(3):268-273.

Higashi, Y. et al., Daily Aerobic Exercise Improves Reactive Hyperemia in Patients with Essential Hypertension. Hypertension, Jan. 1999;33(1):591-597.

Higashi, Y. et al., Regular Aerobic Exercise Augments Endothelium-Dependent Vascular Relaxation in Normotensive as well as Hypertensive Subjects: Role of Enothelium-Derived Nitric Oxide. Circulation, Sep. 1999;100(11):1194-1202.

Hill, C.A. et al., Influence of Beta-Alanine Supplementation on Skeletal Muscle Carnosine Concentrations and High Intensity Cycling Capacity. Amino Acids. Feb. 2007;32(2):225-33, Abstract Only.

Hoffman, J. et al., Effect of Creatine and Beta-Alanine Supplementation on Performance and Endocrine Responses in Strength/Power Athletes. Int J Sport Nutr Exerc. Aug. 2006;16(4):430-446, Abstract Only.

Holm, P.I. et al., Betaine as a Determinant of Postmethionine Load Total Plasma Homocysteine Before and After B-Vitamin Supplementation. Arterioscler Thromb Vasc Biol. Feb. 2004;24(2):301-307.

Hong, H. et al., Effects of Malted Barley Extract and Banaba Extract on Blood Glucose Levels in Genetically Diabetic Mice. J Med Food. 2004 Winter;7(4):487-490, Abstract Only.

Hopkins, W.G. Betaine, Hyperventilation, Hyperimmune Egg Protein and Other Novelties for Performance at the 2007 ACSM Annual Meeting. Sports Sci. 2007;11:1-8, Meeting Abstract Only.

Horwitz, R.D. et al. Effects of Enhanced Ventricular Filling on Cardiac Pump Performance in Exercising Dogs. J Appl Physiol. Dec. 1985;59(6):1886-1890.

Hosoyama, H. et al., Isolation and Quantitative Analysis of the Alpha Amylase Inhibitor in *Lagerstroemia Speciosa* (L.) Pers. (Banaba). Yakugaku Zasshi. Jul. 2003;123(7):599-605, in Japanese, English Abstract Only.

Howe, J.C. et al., Dietary Starch Composition and Level of Energy Intake Alter Nutrition Oxidation in "Carbohydrate-Sensitive" Men. J Nutr. Sep. 1996;126(9):2120-2129.

Jackson, K.G. et al., The Effect of the Daily Intake of Inulin on Fasting Lipid, Insulin and Glucose Concentrations in Middle-Aged Men and Women, British J. Nutrition, 1999, 23-30, vol. 82.

Jarvill-Taylor, K.J. et al., A Hydroxychalcone Derived from Cinnamon Functions as a Mimetic for Insulin in 3T3- L1 Adipocytes, J. Am. College Nutrition, 2001, vol. 20, No. 4, 327-336.

Jentjens, R.L.P.G. et al., High Oxidation Rates from Combined Carbohydrates Ingested During Exercise, Med. Sci. Sports Exercise, 2004, vol. 36, No. 9, 1551-1558.

Jeukendrup, A.E. et al., Oxidation of Carbohydrate Feedings During Prolonged Exercise: Current Thoughts, Guidelines, and Directions for Future Research, Sports Medicine, Jun. 2000, vol. 29(6),407-424.

Jourden, M.J. et al., Changing the Substrate Specificity of Creatine Kinase from Creatine to Glycocyamine: Evidence for a Highly Evolved Active Site. Biochim Biophys Acta. Dec. 2007;1174(12):1519-1527, Abstract Only.

Judy, W.V. et al., Antidiabetic Activity of a Standardized Extract (Glucosol) from Lagerstroemia Speciosa Leaves in Type II Diabetics. A Dose-Dependence Study. J. Ethnopharmacol. Jul. 2003;87(1):115-117, Abstract Only.

Kabir, M. et al., Dietary Amylose-Amylopectin Starch Content Affects Glucose and Lipid Metabolism in Adipocytes of Normal and Diabetic Rats, J. Nutrition, 1998, vol. 128, No. 1, 35-43.

Kannappan, S. et al., Cinnamon Bark Extract Improves Glucose Metabolism and Lipid Profile in the Fructose-Fed Rat. Singapore Med J. Oct. 2006;47(10):858-863.

Kashimura, J. et al., Inhibitory Effect of Palatinose on Glucose Absorption in Everted Rat Gut. J Nutr Sci Vitaminol. Feb. 2007;53(1):87-89, Abstract Only.

Kashimura, J. et al., New Findings of Palatinose Function. Proc. Res Soc Jpn Sugar Refin. Tech. 2003;51:19-25, English Abstract Only.

Kawai, K. et al., Changes in Blood Glucose and Insulin After an Oral Palatinose Administration in Normal Subjects, Endocrinologia Japonica, 1985, 933-936, vol. 32(6), Abstract Only.

Khan, A. et al., Cinnamon Improves Glucose and Lipids of People with Type 2 Diabetes. Diabetes Care. Dec. 2003;26(12):3215-3218.

Kim, S.H. et al., Anti-Diabetic Effect of Cinnamon Extract on Blood Glucose in db/db Mice, J Ethnopharmacol. Mar. 2006;104(2):119-123, Abstract Only.

Klein, G. et al., Antidiabetes and AnTI-Obesity Activity of *Lagerstroemia speciosa*. Evid. Based Complement Alternat Med. Dec. 2007;4(4):401-407.

Kreider, R.B. et al., Effects of Phosphate Loading on Metabolic and Myocardial Responses to Maximal and Endurance Exercise. Int J Sport Nutr. Mar. 1992;2(1):20-47, Abstract Only.

Lacerda, A.C.R. et al., Carbohydrate Ingestion During Exercise Does Not Delay the Onset of Fatigue During Submaximal Cycle Exercise, J. Strength & Conditioning Research, 2009, 1276-81, vol. 23(4).

Larsen, F.J. et al., Effects of Dietary Nitrates on Oxygen Cost During Exercise. Acta Physiol. Sep. 2007;191(1):59-66, Abstract Only.

Larsen, S.D. et al., Synthesis and Biological Activity of Analogues of the Antidiabetic/Antiobesity Agent 3-Guandionproponionic Acid: Discovery of a Novel Aminoguanidinoacetic Acid Antidiabetic Agent. J Med Chem. Apr. 2001;44(8):1217-1230, Abstract Only.

Latzka, W.A. et al., Hyperhydration: Thermoregulatory Effects During Compensable Exercise-Heat Stress. J Appl Physiol. Sep. 1997;83(3):860-866.

Lina, B.A.R. et al., Isomaltulose (Palatinose): A Review of Biological and Toxicological Studies, Food & Chemical Toxicology, 2002, vol. 40, 1375-1381.

(56) References Cited

OTHER PUBLICATIONS

Liu, F. et al., Extract of *Lagerstroemia speciosa* L. has Insulin-Like Glucose Uptake-Stimulatory and Adipocyte Differentiation-Inhibitory Activities in 3T3-L1 Cells. J Nutr. Sep. 2001;131(9):2242-2247.

Lucotti, P. et al., Beneficial Effects of a Long Term Oral L-Arginine Treatment Added to a Hypocaloric Diet and Exercise Training in Obese, Insulin-Resistant Type 2 Diabetic Patients. Am J Physiol Endocrinol Metab. Jun. 2006;291 (5):E906-E912.

Luetkemeier, M.J. et al., Hypervolemia and Cycling Time Trial Performance. Med. Sci. Sports. Exerc. Apr. 1994;26(4):503-509.

Lyons, T.P. et al., Effects of Glycerol-Induced Hyperhydration Prior to Exercise in the Heat on Sweating and Core Temperature. Med Sci Sports Exerc. Aug. 1990;22(4):477-483, Abstract Only.

Maeda, S. et al., Moderate Regular Exercise Increases Basal Production of Nitric Oxide in Elderly Women. Hypertens Res. Dec. 2004;27(12):947-953.

Manal, N. What is Inulin Made From? eHow, Apr. 2010, http://www.ehow.com/about_5170488_inulin-made-from_.html.

Mang, B. et al., Effects of a Cinnamon Extract on Plasma Glucose, HbA, and Serum Lipids in Diabetes Mellitus Type 2. Eur J Clin Invest. May 2006;36(5):340-344, Abstract Only.

McConnell, G.K. et al., L-Arginine Infusion Increases Glucose Clearance During Prolonged Exercise in Humans. Am J Physiol Endocrinol Metab. Jan. 2006;290(1):E60-E66.

Meglasson, M.D. et al., Antihyperglycemic Action of Guanidinoalkanoic Acids: 3-Guanidinopropionic Acid Ameliorates Hyperglycemia in Diabetic KKAy and C57BL6Job/ob Mice and Increases Glucose Disappearance in Rhesus Monkeys. J Pharmacol Exp Ther. Sep. 1993;266(3):1454-1462, Abstract Only.

Melse-Boonstra, A. et al., Betaine Concentration as a Determinant of Fasting Total Homocysteine Concentrations and the Effect of Folic Acid Supplementation on Betaine Concentrations. Am J Clin Nutr. Jun. 2005;81(6):1378-1382.

Mirshamsi, S. et al., BVT.3531 Reduces Bodyweight and Activates K(ATP) Channels in Isolated Arcuate Neurons in Rats. Regul. Pept. Jun. 2007;141(1-3):19-24, Abstract Only.

Misner, B. Endurance Nutrition: How and What to Eat Before, During, and After Exercise? Pre-Event Meal Warning: Eat 3 Hours Before Exercise, AFPA Articles and Newsletters, 2010, http://www.afpafitness.com/articles/articles-and-newsletters/research-articles-index/athletes-sports-conditioning/endurance-nutrition-how-and-what-to-eat-before-during-and-after-exercise-pre-event-meal-warning-eat-3-hours-before-exercise/.

Montner, P. et al., Pre-Exercise Glycerol Hydration Improves Cycling Endurance Time. Int J Sports Medicine. Jan. 1996;17(1):27-33, Abstract Only.

Murray, R. et al., Physiological Responses to Glycerol Ingestion During Exercise. J. Appl Physiol. Jul. 1991;71(1):144-149, Abstract Only.

Nandhini, D. et al., Insulin-Like Effects of Bis-Glycinato Oxovandium(IV) Complex on Experimental Diabetic Rats. Indian J. Biochem Biophys. Feb. 1993;30(1)73-76, Abstract Only.

Nazar, K. et al., Phosphate Supplementation Prevents a Decrease of Triiodothyronine and Increases Resting Metabolic Rate During Low Energy Diet. J Physiol Pharmacol. Jun. 1996;47(2):373-383, Abstract Only.

Niness, K.R., Inulin and Oligofructose: What are They? J Nutr. Jul. 1999;129(Suppl 7):1402S-1406S.

O'Brien, C. et al., Glycerol Hyperhydration: Physiological Responses During Cold-Air Exposure. J Appl Physiol. Aug. 2005;99(2):515-521.

Ohira, Y. et al., Non-Insulin and Non-Exercise Related Increases of Glucose Utilization in Rats and Mice. Jpn J Physiol. 1994;44(4):391-402.

Oizumi, T. et al., A Palatinose-Based Balanced Formula Improves Glucose Tolerance, Serum Fatty Acid Levels and Body Fat Composition. Tohoku J Exp Med. Jun. 2007;212(2):91-99.

Olthof, M.R. et al., Effects of Betaine Intake on Plasma Homocysteine Concentrations and Consequences for Health. Curr Drug Metab. Feb. 2005;6(1):15-22, Abstract Only.

Olthof, M.R. et al., Low Dose Betaine Supplementation Leads to Immediate and Long Term Lowering of Plasma Homocysteine in Healthy Men and Women. J Nutr. Dec. 2003;133(12):4135-4138.

Paddon-Jones, D. et al., Amino Acid Ingestion Improves Muscle Protein Synthesis in the Young and Elderly. Am J Physiol Endocrinol Metab. Mar. 2004;286(3):E321-E328.

\* cited by examiner

METHOD AND COMPOSITION FOR IMPROVED MUSCLE PERFORMANCE

This application claims the benefit of earlier filed U.S. Patent Application Ser. No. 61/179,272 filed on 18 May 2009 which is hereby incorporated by reference.

FIELD OF THE INVENTION

A method for the regulation of athletic function or muscle performance involving the use of a nutritional composition containing fast and slow absorbing carbohydrates in combination with an insulinomimetic compound is disclosed. By providing a combination of fast and slow absorbing carbohydrates in conjunction with an insulinomimetic compound for oral ingestion, regulation of insulin dependent pathways can be affected to promote increased glycogen conservation, resynthesis, and/or storage.

BACKGROUND

An adult human weighing 70 kg, with average physical activity, requires about 2400-2900 kcal from metabolic fuels each day to maintain basal metabolic functions. The requirement for metabolic fuels is generally constant throughout the day. However, if the intake of carbohydrates is lower than energy expenditures, such as may be the case during intense or prolonged physical activity, glucose derived from ingested carbohydrates is spared for use by the central nervous system and erythrocytes, and glycogen stores are mobilized to provide energy to muscle tissue.

Glycogen is the major storage carbohydrate in mammals and is a branched polymer of α-D-glucose. It occurs mainly in the liver and muscle tissue, with a proportionately greater amount occurring in muscle tissue because of its greater overall mass in the body. In the liver, glycogen's major function is to provide glucose for extrahepatic tissues. In muscles, it serves mainly as a ready source of metabolic fuel.

Glycogen is synthesized from glucose by the pathway of glycogenesis and is broken down into glucose-6-phosphate and, ultimately, glucose by a separate pathway known glycogenolysis. Glycogenolysis leads to glucose formation in the liver and lactate formation in muscle owing to the respective presence or absence of glucose-6-phosphatase. Cyclic adenosine monophosphate (cAMP) integrates the regulation of glycogenolysis and glycogenesis by promoting simultaneous activation of phosphorylase and inhibition of glycogen synthase.

Glucose uptake into the muscle tissue is controlled by insulin which is secreted by the B islet cells of the pancreas in response to an increased concentration in the portal blood. An early response to insulin in muscle tissue is the migration of glucose transporter vehicles to the cell surfaces, exposing active glucose transporters (GLUT 4). These insulin-sensitive tissues will generally only take up glucose from the blood stream in any significant extent in the presence of insulin. As insulin secretion falls, the transporters are internalized again reducing glucose uptake.

Insulin acts reciprocally by inhibiting glycogenolysis and stimulating glycogenesis. Insulin is secreted in direct response to high blood glucose levels and stimulates the liver to store glucose as glycogen (glycogenesis). As blood glucose levels fall glucagon secretion by the pancreas increases stimulating the break down of glycogen into glucose (glycogenolysis). Large intakes of carbohydrates about 30-60 minutes prior to exercise may have a detrimental effect on performance by causing an elevation of insulin pushing glucose into the cells and consequently inhibition of fatty acid mobilization. If less fat is available to the muscles, the limited glycogen stores will be used at a faster rate, thus hastening the onset of fatigue. During exercise, insulin secretion is inhibited, thus the ingestion of carbohydrates during exercise does not inhibit fat mobilization and may improve performance. However, the lack of insulin promotes glycogenolysis or the depletion of glycogen stores which can lead to fatigue.

The hallmarks of insulin action are the stimulation of anabolic responses and suppression of catabolic responses. These responses are orchestrated by the insulin pathway and are initiated by the binding of insulin to the insulin receptor. In patients with diabetes mellitus the body either does not produce insulin (Type I) or the body cannot use insulin properly (Type II) with insulin resistance playing a key role in the development of the disease. Symptoms of insulin resistance include a decreased stimulation of muscle glycogen synthesis (glycogenesis) and defects in glycogen synthase activity, hexokinase activity, and glucose uptake.

Generally, physical training enhances insulin-stimulated glucose disposal in proportion to the improvement in physical fitness. Further, athletes are typically more sensitive to insulin. Thus, even with ingestion of small amount of simple carbohydrates, athletes can experience a spike in insulin secretion which can speed the depletion of glucose in the blood stream which in turn signals the reduction in insulin production. However, as noted above, once blood glucose levels begin to fall, glucose is spared for use by the central nervous system and erythrocytes, while skeletal tissue turns to glycogen stores and glycogenolysis.

Accordingly, there is a need and/or a desire for a method of enhancing muscle performance which provides both a supply of glucose to muscle tissue at the start of exercise or athletic activity and a steady supply of glucose to muscle tissues during physical activity to promote glycogen conservation, storage, and/or resynthesis and which avoids or offsets the consequences of insulin spikes resulting from the ingestion of carbohydrates and/or the inhibition of insulin production during physical activity.

SUMMARY

The presently claimed invention relates to a method for the regulation of blood glucose levels and for the promotion of muscle performance via oral ingestion of a nutritional composition including selected carbohydrates to promote steady release of glucose into the blood stream coupled with an agent to promote steady transport of glucose into muscle tissue. The method includes administering to humans an effective amount of a nutritional composition containing fast and slow absorbing carbohydrates in combination with one or more insulinomimetic compounds. The composition can include moderate to fast absorbing carbohydrates such as, but not limited to, amylopectin, dextran, and/or maltodextrin, slow absorbing carbohydrates including, but not limited to, isomaltulose and/or inulin, which, in combination with one or more insulinomimetic compounds such as, for example, methylhydroxychalcone polymers, vanadium oxoanions and complexes, and corosolic acid, results in a moderate glucose release after ingestion. The fast and slow absorbing carbohydrates can be present in a ratio of 2:1 based on a total weight of the carbohydrates in the formulation. Additional ingredients or compounds which can be included in the nutritional composition included free amino acids, creatine precursors, creatine transport agents, and/or electrolytes.

For the most part, athletes or persons engaged in regular or prolonged physical activity perform better when consuming a moderate glucose release beverage during exercise as compared to a fast glucose release beverage. Such improvement in performance is believed to be associated with the provision of nutritional support at the start or beginning of physical activity while avoiding sudden drops or spikes in glucose levels throughout or over the course of the physical activity. A moderate glucose release rate can be achieved by combining carbohydrates with varying absorption rates. The ability and rate at which the body can spare and replenish muscle glycogen is critical for physical performance. In addition, the aforementioned nutritional composition may also allow an end user to achieve one or more beneficial results such as, for example, enhanced or increased glycogen supercompensation, muscle cell or myocellular expansion, and/or peak power output, hyperaminoacidemia, increased protein synthesis, and/or improved energy metabolism.

The aforementioned nutritional composition may further allow an end user to achieve one or more beneficial results including anabolism, anti-catabolism, increased strength, improved recovery, and enhanced endurance, mental focus hydration and/or recovery between sets and after exercise.

As used herein it is understood that the term "amylopectin" also includes derivatives of amylopectin including, but not limited to, varying molecular weights, as well as other derivatives including derivatives that become active after or during metabolism.

As used herein it is understood that the term "dextran" also includes derivatives of dextran including, but not limited to, dextran chelates, dextran esters, varying molecular weights of dextran, as well as other derivatives including derivatives that become active after or during metabolism.

As used herein it is understood that the term "inulin" or "inulins" include inulin polymers with a terminal glucose unit (i.e., alpha-D-glucopyranosyl-[beta-D-fructofuranosyl] (n−1)-D-fructofuranosides or GpyFn) and without a terminal glucose unit (i.e., beta-D-fructocpyranosyl-[D-fructofuranosyl](n−1)-D-fructofuranosides nor FpyFn) which can be derived from any suitable natural or synthetic source.

As used herein the term "fast absorbing carbohydrate" refers to carbohydrates having a glycemic index value of 70 or above while term "slow absorbing carbohydrate" refers to carbohydrates having a glycemic index value of 55 or less. Accordingly, "moderately absorbing carbohydrates" refer to carbohydrates having a glycemic index value falling between 55 and 70. The glycemic index of a carbohydrate is defined as the area under the two hour blood glucose response curve (AUC) following the ingestion of a fixed portion of glucose (usually 50 g). The AUC of the test carbohydrate is divided by the AUC of the standard (glucose) and multiplied by 100. The current validated methods use glucose as the reference food, giving it a glycemic index value of 100 by definition.

As used herein the terms "athlete" refers to mammals such as human individuals who regularly engage in physical activity particularly activities generally classified as aerobic activities, individuals who engage in prolonged or extended physical activities such as, for example, long distance running or walking, hiking or biking, and/or individuals who engage in regular resistance or weight training.

As used herein the terms "'steady' or 'moderate' release of glucose" refers to a rate which provides an average blood glucose level of about 90 milligrams/deciliter (mg/dl) to about 120 mg/dl over a given period of time.

DETAILED DESCRIPTION

The object of the claimed invention can be obtained by administering to an individual a nutritional composition containing a carbohydrate source which provides a steady supply of glucose to the muscles in conjunction with an insulinomimetic compound.

In accordance with one embodiment, a method for conserving and/or promoting synthesis of glycogen includes administering to an individual engaging in physical activity an effective amount of a nutritional composition including a carbohydrate source which provides a steady supply of carbohydrates to the blood stream. The carbohydrate source includes at least two glucose polymers having different release rates in the digestive track to provide an overall moderate or sustained release of glucose to the cells. The nutritional composition may allow the end user to achieve one or more beneficial results including increased glycogen supercompensation, hyperaminoacidemia, increased protein synthesis, muscle cell or myocellular expansion, increased peak power output, or enhanced energy metabolism. Still further, the nutritional composition may allow the user to achieve one or more beneficial results such as anabolism, anti-catabolism, anti-fatigue, and improved strength, endurance, mental focus, hydration and/or recovery between sets and after exercise.

Carbohydrates are an essential macronutrient consisting of starches, sugars, cellulose, gums, and the like. Carbohydrate is the usually predominate macronutrient in the human diet and is utilized for immediate and long-term energy. Ingested carbohydrate is metabolized or broken down to glucose in the body then stored in the liver and muscle as glycogen via the production of insulin from the pancreas. Anaerobic and aerobic exercise relies on stored glycogen for energy and thus the greater the amount of glycogen the greater the potential for enhanced or improved physical performance. The amount of glycogen in the muscle also contributes to the aesthetics of the physique because every one gram of stored glycogen holds three grams of intracellular water and nutrients. This will cause a lean muscle to look rounder and feel fuller.

Suitably, the nutritional composition includes a combination of fast and slow absorbing carbohydrates and, optionally, a moderately absorbing carbohydrate. Advantageously, the carbohydrates utilized in the nutritional composition having differing rates of absorption provide for a steady release of glucose from the gastrointestinal tract.

The human diet contains various types of carbohydrate including common starches, which are typically comprised of approximately thirty percent amylose and seventy percent amylopectin, monosaccharides such as glucose and fructose, disaccharides such as sucrose, polysaccharides, and oligosaccharides. Some carbohydrates may be in the form of digestible, indigestible, soluble, and/or insoluble fibers which are typically classified as poly- or oligosaccharides. Examples of polysaccharides commonly found in the human diet include amylase, an essentially a linear polysaccharide with molecules consisting of 200 to 20,000 glucose units which form a helix, and amylopectin, a highly branched chain carbohydrate.

In accordance with one embodiment, the carbohydrate source includes a combination of amylopectin to support conservation and/or promote synthesis of glycogen in the muscles and a dextran polymer to support conservation and/or promote synthesis of glycogen in the liver.

Amylopectin is a highly branched chain carbohydrate having a backbone consisting of a plurality of glucose residues connected by alpha-(1→4) glycosidic linkages. Branching along the backbone occurs with alpha-(1→6) glycosidic linkages occurring about every 24 to 30 glucose units. The molecular weight of amylopectin may reach as high as eighty million. Pure amylopectin is believed to promote glucose and amino acid uptake into the muscle thereby promoting anabolism, protein synthesis, and muscle cell expansion. Muscle cells typically attract three grams of fluid (i.e. water) for every one gram of glycogen stored in the muscle in addition to the vitamins, minerals, bioactive food ingredients and various nutrients present in the fluid thus creating a nutrient dense, muscle promoting myocellular expansion or growth.

Dextran is carbohydrate and glucan that, while similar to amylopectin, is not typically utilized as an oral ergogenic aid. Dextran is a high molecular weight branched chain glucose polymer produced by the fermentation of sucrose and found in beverages such as water kefir. The main chains of dextran are formed by alpha-(1→6) glycosidic linkages and the side branches are attached by alpha-(1→4) glycosidic linkages. Dextran is an extremely versatile carbohydrate with a plethora of uses such as direct food additive, indirect food additive, intravenous plasma expander, and dietary supplement or myocellular expander. Dextran is sold as a direct food additive in the European Union in baked goods such as pastries, cakes, and muffins. The intravenous use of various types of dextran causes plasma expansion because large dextrans cannot pass out of the vessels and thus act as osmotic agents. The oral use of dextran for the regulation of athletic function in athletes is believed to foster glycogen supercompensation without excessive carbohydrate depletion and loading. Dextran and amylopectin are believed to work synergistically and thus provide a superior form of ingestible carbohydrate for the promotion of glycogen resynthesis and supercompensation.

The proper form of dextran is critical to its oral absorption, bioavailability, and effectiveness. Dextran polymers are available in multiple molecular weights ranging from 10,000 Daltons (Da) to 150,000 Daltons. Dextran polymers included in the nutritional composition should be compatible with oral consumption. Dextran with a molecular weight of 16,000,000 has been shown to possess poor oral absorption, whereas dextran with a molecular weight of 40,000 has been shown to possess superior oral absorption.

The relative amounts of amylopectin and dextran can be selected in order to provide a profiled release of glucose from the gastrointestinal tract. In other words, the relative amounts of amylopectin and dextran can be selected such that peak glucose absorption times of the two polymers are offset.

The carbohydrate source can further include maltodextrin, a glucose polymer typically composed of mixtures of chains that vary from three to nineteen glucose units long. The amount of maltodextrin included in the carbohydrate source can vary depending upon whether a moderate or fast glucose absorption rate is desired or needed to balance the absorption profile of the carbohydrate source to achieve a moderate or steady overall glucose release rate from the gastrointestinal tract.

The carbohydrate source can still further include isomaltulose, a glucose/fructose disaccharide that is commercially produced enzymatically from beet sugar and/or sucrose. Enzymatic re-arrangement of the alpha-(1→2) glycosidic bond between the glucose and the fructose molecule to an alpha-(1→6) glycosidic bond converts sucrose into isomaltulose. Isomaltulose is also a natural component of honey and sugar cane molasses.

Isomaltulose, or Palatinose® as it is commonly known, was discovered in 1957 by the research and development department of Stidzucker AG. The name Palatinose® comes from the Palatinate where it was discovered; this region of Germany was known as "Palatinum" by the Romans. Isomaltulose is a slow releasing (Low Glycemic Response), lipolytic (fat burning), and nootropic (smart) carbohydrate providing sustained energy and promoting mental focus for enhanced physical performance. The addition of isomaltulose is designed to provide a steady state release of carbohydrate during training allowing the other carbohydrates to initiate muscle glycogen resynthesis. Isomaltulose releases from the stomach slowly due to its chemical structure and metabolic breakdown. Suitably, as the amount of glucose derived from the first, fast releasing glucose polymer declines from a first absorption peak an amount of glucose released from a second slow releasing glucose increases as it approaches a second, later peak absorption time to provide a steady average rate of glucose release.

The amount of isomaltulose included in the carbohydrate source can be varied as desired or needed to balance the absorption profile of the carbohydrate source to achieve a moderate overall glucose release rate from the gastrointestinal tract.

In accordance with another embodiment, the carbohydrate source can include a combination of amylopectin and inulin and, optionally, maltodextrin and/or isomaltulose.

Inulin or inulins are polysaccharides classified as fructans which are typically derived from the root or rhizomes of plants which do not synthesize and store starch. Examples of such plants include, but are not limited to elecampane (*Inula racemosa*), dandelion (*Taraxacum officinale*), wild yam (*Dioscorea* spp.), Jerusalem artichoke (*Helianthus tuberoses*), chicory (*Cichorium intybus*), jicama (*Pachyrhizus erosus*), onion (*Allium cepa*), burdock (*Arctium lappa*), garlic (*Allium sativum*), agave (*Agave* spp.), yacón (*Samallanthus sonchifolious* spp.), and camas (*Camassia* spp.). Inulin polymers are composed mainly of 10 to several thousand fructose units joined by beta-(2→1) glycosidic bonds which may or may not include a glucose terminal unit. Inulins with a terminal glucose unit are known as alpha-D-glucopyranosyl-[beta-D-fructofuranosyl](n−1)-D-fructofuranoside while inulins without a terminal glucose unit are known as beta-D-fructopyranosyl-[D-fructofuranosyl](n−1)-D-fructofuranosides.

Inulin's flavor can range from bland to subtly sweet (i.e., about 10% the sweetness of sucrose). Due to its structural characteristics, inulin contains only about 25% to about 33% of the food energy provided by sugar or other carbohydrates mainly because inulins are resistant to breakdown by the human enzymes ptyalin and amylase which are adapted to digest starches. As a result, inulin is only minimally digested in the upper gastrointestinal tract with metabolism and absorption occurring predominantly in the lower gastrointestinal tract and colon. Accordingly, inulins are typically classified as slow absorbing carbohydrates.

In general, to provide a steady supply of glucose to blood stream, the carbohydrate source can include a combination of fast absorbing carbohydrates and slow absorbing carbohydrates in a ratio of 2:1 based on a total weight of the carbohydrate source. In accordance with another embodiment, the carbohydrate source can include about 65% to about 75% by weight fast absorbing carbohydrate and about 25% to about 35% by weight slow absorbing carbohydrates based on a total weight of the carbohydrate source. In accordance with a further embodiment, the carbohydrate source can include about 70% by weight fast absorbing carbohydrate and about 30% by weight about slow absorbing carbohydrates based on a total weight of the carbohydrate source.

Suitably, the nutritional composition can include about 15 grams to about 45 grams of the carbohydrate source per serving. Individual carbohydrates can be present in amounts ranging from about 1 milligrams (mg) to about 10,000 mg. In accordance with certain embodiment, amylopectin, maltodextrin, and/or isomaltulose can each be present in the nutritional composition in an amount ranging from about 1 mg to about 10,000 mg while dextran and/or inulin can be present in an amount ranging from about 1 mg to about 5,000 mg.

Generally, if glycogen stores are spared or conserved during exercise it is easier for an organism to resynthesize or increase glycogen stores after exercise. It is believed that providing carbohydrates (i.e., glucose) at a controlled and/or steady rate during exercise can provide a sufficient amount of glucose to fuel cells, particularly muscle cells, and can also promote glycogen production. Further, it is believed that sparing or conserving glycogen stores during exercise can promote supercompensation (i.e., storage of elevated amounts of glycogen) post-exercise. Increasing the amount of glycogen stored in the muscles and/or liver (supercompensation) can result in improved or enhanced muscle performance during subsequent training and/or athletic events.

As noted above, insulin reciprocally promotes the formation of glycogen (glycogenesis) in the liver and muscles and inhibits the breakdown of glycogen (glycogenolysis) into glucose. Insulin also inhibits fatty acid mobilization which decreases the amount of fat available to the muscles thereby increasing the rate at which glycogen stores in the muscles are consumed leading to fatigue. However, the secretion of insulin is typically inhibited during exercise in order to promote the release of glucose and the consequent production of adenosine triphosphate (ATP), the main energy source for cells.

The carbohydrate source is administered in conjunction with an insulin mimetic or insulinomimetic compound during exercise in order to offset the reduction in insulin secretion and promote glycogen conservation and/or synthesis. Such insulin mimetics and amounts thereof included in the nutritional composition can be selected to have minimal impact on fatty acid mobilization, assist in or enhance the absorption of carbohydrates and amino acids from the gastrointestinal tract. Insulinomimetic compounds can also decrease actual insulin production and/or prevent or reduce the insulin spike which typically occurs in response to elevated glucose levels.

In general, a spike in blood insulin concentrations is undesirable for athletes because insulin pushes glucose into the cells and inhibits fatty acid mobilization leaving less fat available to the muscles as an energy source. If less fat is available, the limited glycogen stores will be used at a faster rate hastening the onset of fatigue. However, insulinomimetics alone are not suited to reducing or ameliorating insulin spikes in response to increased blood glucose levels in athletes because the level needed to achieve such an affect can cause gastric upset and other undesirable side effects. Further, athletes are generally more sensitive to insulin and thus at greater risk for experiencing an insulin spike upon the ingestion of a glucose source. In contrast, the combination of fast and slow absorbing carbohydrates with an insulinomimetic compound meets this need by providing a steady release of carbohydrates to the blood stream while muting or reducing insulin release.

Suitable insulin mimetics which can be utilized in the nutritional composition include, but are not limited to: cinnamon extracts which can include methylhydroxychalcone polymers; vanadium oxoanions and complexes such as bis (picolinato)oxovanadium and bis(glycinato)oxovanadium; banaba plant extracts; and corosolic acid.

One suitable cinnamon extract material which may be included in the nutritional composition is available under the tradename Cinnulin PF®. Cinnulin PF® is an aqueous extract of cinnamon bark, which contains uniquely linked proanthocyanidins, or ULPs. Proanthocyanidins are natural flavonoids found in cinnamon, grape seed, red wine, cranberry and green tea, etc. Researchers have found that ULPs are powerful antioxidants that eliminate harmful free radicals and may promote glucose metabolism. Clinical studies report that Cinnulin PF® decreases blood glucose (sugar), cholesterol and triglyceride levels. The regulation of insulin plays an important role in the storage of carbohydrate in muscle in the form of glycogen.

Vanadium is a metallic element, which exists in several oxidation states and is known for its unique colors. Vanadium is found in foods such as skim milk, lobster, vegetable oils, many vegetables, grains and cereals. Vanadium is also known for its insulinomimetic functions and, therefore, for its ability to regulate blood glucose levels. The first form of vanadium sold as a dietary supplement consisted of the sulfate salt or vanadyl sulfate. The next generation vanadium includes complexes such as bis(glycinato)oxovanadium (BGOV) and bis (picolinato)oxovanadium (BPOV), which possess greater absorption and bioavailability than the sulfate salt. Bis(glycinato)oxovanadium (BGOV) is a complex of vanadium and the amino acid glycine while bis(picolinato)oxovanadium (BPOV) is a complex of vanadium and picolinic acid.

Banaba, also known as *Lagerstroemia speciosa*, Crepe Myrtle, Queen's Flower or Pride of India, is a tropical botanical which contains the triterpene corosolic acid. Corosolic acid is thought to regulate or modulate insulin, which regulates blood sugar levels. Banaba research demonstrates the regulation of glucose transport in cell cultures and modulation of glucose in animals. There is also human research supporting the regulation of blood glucose. However, new research has recently demonstrated there may be other constituents of banaba, which are also involved in the glucose transport function. Currently the blood sugar regulating properties of corosolic acid are thought to be involved in the modulation of hepatic or liver glucose metabolism. In accordance with certain embodiments, an extract of the leaves of the banaba plant standardized to contain 18% corosolic acid can be used in the nutritional composition.

The amount of carbohydrate source and/or the amount of insulin mimetic can vary depending upon the desired outcome. Generally, a ratio of carbohydrate to insulin mimetic is established that provides both a steady rate of release of glucose into the gastrointestinal tract and a steady rate of absorption of glucose by the cells. Suitably, an amount of insulin mimetic included in the nutritional composition is selected to provide an absorption response that is greater than or equal to a high insulin response. However, the concentration or amount of insulinomimetic compounds included in the nutritional composition should be maintained at a level which does not result in adverse or undesirable side effects following ingestion such as for example, gastric upset, hypoglycemia, and/or glycosuria.

In accordance with certain embodiments, the nutritional composition can include one or more insulinomimetic compounds in the following concentrations per serving: about 1 mg to about 500 mg methylhydroxychalcone polymers and/or an amount of an extract of cinnamon including about 1 mg to about 500 mg methylhydroxychalcone polymers; about 1 microgram (mcg) to about 2 milligrams of a vanadium oxoanion or complex such as BGOV or BPOV; and/or about 1 mcg to about 15 mg of corosolic acid and/or an amount of an extract of *Lagerstoemia speciosa* containing about 1 mcg to about 15 mg of corosolic acid. In accordance with one embodiment, the nutritional composition can include the carbohydrate source and the insulinomimetic compound(s) in a ratio of about 150:1 by weight.

The nutritional composition can further include one or more free amino acids including essential amino acids and/or branched chain amino acids. Generally, it has been found that ingesting carbohydrates in combination with free amino acids has a beneficial impact on muscle performance and recovery. For example, one study demonstrated that consuming a 6% carbohydrate solution with 6 grams of essential amino acids had an anabolic effect stimulating protein synthesis during exercise without compromising glycogen stores. Additionally, amino acids have been shown to support glycogen resynthesis in the post-exercise period. Further, essential amino acids have generally been shown to have both an anti-catabolic effect and an anabolic effect during exercise and in the post-exercise period while branched chain amino acids (BCAAs), particularly leucine, have been shown to preserve muscle and decrease protein breakdown during times of weight loss or other catabolic circumstances.

Free amino acids which can be utilized in the nutritional composition include, but are not limited to, essential amino acids selected from histidine, methionine, phenylalanine, lysine, threonine, and combinations thereof, and branched chain amino acids (BCAAs) selected from isoleucine, leucine, valine, and combinations thereof, and/or salts, analogues, esters, ethers, and derivatives thereof. For example, the free essential amino acids included in the nutritional composition can include hydrochloride salts such as, but not limited to, histidine hydrochloride, methionine hydrochloride, phenylalanine hydrochloride, lysine hydrochloride, threonine hydrochloride, and combinations thereof.

The essential amino acids histidine, methionine, threonine, lysine, phenylalanine, leucine, isoleucine, and valine are amino acids not made by the body and must be consumed from food or supplements. The nutritional composition and methods disclosed herein take full advantage of the ergogenic benefit of combining carbohydrates and essential amino acids.

The nutrient timing or the ingestion of certain nutrients at specific times such as essential amino acids is critical for maximum anabolism and physical performance. In fact, the combination of carbohydrate and essential amino acids during and immediately post workout creates an anabolic response resulting in stimulation of mammalian target of rapamycin (mTOR) and muscle protein synthesis in humans. mTOR is a protein kinase or enzyme which is a regulator of protein synthesis and muscle growth. The simultaneous ingestion of both essential amino acids and carbohydrates during resistance exercise as compared to carbohydrate or essential amino acids ingested separately has been shown to promote a significantly greater anabolic response. The ingestion of both essential amino acids and carbohydrates may regulate exercised induced cortisol, muscle degradation, and/or anti-catabolic responses, and promote insulin release, anabolism, and/or overall physical performance.

Branched chain amino acids consumed during and post workout are thought to spare muscle glycogen, promote anabolism, anti-catabolism, recovery, alanine and glutamine production, and regulate fatigue (lactic acid) and DOMS (Delayed Onset Muscle Soreness).

In accordance with certain embodiments, the nutritional composition may include one or more salts of a branched chain amino acid. Suitable BCAA salts include, but are not limited to, isoleucine alpha amino-N-butyrate, isoleucine nitrate, leucine alpha amino-N-butyrate, leucine nitrate, valine alpha amino-N-butyrate, and valine nitrate.

It is generally believed that consumption of carbohydrates in conjunction with one or more BCAA salts has a glycogen sparing effect during exercise. Such action may be, in part, due to the action and/or contribution of the salt anion to various metabolic processes. For example, BCAA salts are generally more bioavailable (i.e., more readily absorbed from the gastrointestinal tract) than the pure BCAA forms.

The branched chain amino acid leucine is metabolized to ketoisocaproate (KIC) and metabolized further to beta-hydroxy-beta-methylbutyrate (HMB). These leucine metabolites are known for their physical enhancement benefits and have been successfully sold as ergogenic dietary supplements for many years. However, one unknown leucine metabolite referred to as alpha-amino-N-butyrate appears to be a powerful ergogenic aid and anti-catabolic. Alpha-amino-N-butyrate, an amino fatty acid metabolite of leucine, is a non-essential amino acid which serves as a transaminative product of 2-Oxobutyrate and may spare the demand for leucine as they are structurally similar and can compete for uptake. Further, alpha-amino-N-butyrate may function to increase hemoglobin content and can work to increase the oxygen carrying capacity of the body which in turn promotes lean body mass enhancement and preservation of muscle.

Nitrate, a salt of nitric acid ($NO^-_3$), is a natural constituent of plants and is found in vegetables at varying levels. According to the World Health Organization, most adults ingest 20-70 milligrams of nitrate per day with most of this coming from foods like lettuce, celery, beets, and spinach. Oral nitrate consumption from vegetables has been studied and linked to the promotion of cardiovascular health. Dietary nitrate is converted to nitrite ($NO^-_2$), which may lead to the formation of nitric oxide. Nitric oxide has been demonstrated to have various performance benefits including enhanced vasodilation which promotes improved blood flow and oxygen transport to cells. Dietary nitrate has also been shown to lower oxygen demand during submaximal exercise thus demonstrating enhanced energy production, which supports the use of nitrates as performance enhancing ergogenic aids. The branched chain amino acid nitrates possess multi-functionality. The amino acid nitrate salt may improve oral absorption while simultaneously enhancing nitric oxide production and physical performance.

The nutritional composition can still further include one or more phosphate polymers. Suitable phosphate polymers include, for example, glycerophosphate polymers such as calcium, magnesium, potassium, and sodium glycerophosphate. Glycerophosphate polymers are advantageously employed in the nutritional composition because they both support hydration and provide phosphate substrates for the synthesis of glycogen.

Glycerol hyper-hydration is a technique utilized by athletes to promote super hydration prior to an event in order to regulate hydration during hot or cold conditions (loss of fluids), thermoregulation (body temperature), and promote endurance.

Oral phosphate loading is another method to promote athletic performance or endurance. Athletes consume mineral phosphates for three days prior to an event or competition in order to load muscle phosphate levels thus supporting ATP recycling and possibly promote the up regulation of DPG (2,3-diphosphoglycerate), which may allow for improved unloading of oxygen from red blood cells.

Adequate electrolytes or plasma and tissue minerals are critical for optimal athletic performance. Loss of minerals during prolonged exercise via sweating can have a negative impact on physical performance. Athletes slow down or decrease physical performance by two percent for every one percent loss of body weight due to sweating or loss of fluids.

Calcium is one of the most important minerals for growth, maintenance, and reproduction in the human body. Calcium is important for heart function, and helps with muscle contraction, nerve signaling, and regulates muscle cramping due to intense exercise. Magnesium plays an important role in the production and transport of energy. It is also important for the contraction and relaxation of muscles. Magnesium is involved in the synthesis of protein, and it assists in the functioning of certain enzymes in the body and regulates muscle cramping due to intense exercise. Potassium has various roles in metabolism and body functions and is essential for the proper function of all cells, tissues, and organs. Potassium assists in the regulation of the acid-base balance, assists in protein synthesis from amino acids, carbohydrate metabolism and it is necessary for the building of muscle and for normal body growth. Sodium regulates blood pressure and blood volume, is crucial for the functioning of muscles and nerves, promotes creatine transport, and may be the most critical mineral in the regulation of muscle cramping due to intense exercise.

Additional components or compounds which can be utilized in the nutritional composition include: other carbohydrates such as, for example, inulin or fructooligosaccharide; effervescent delivery agents such as, for example, bicarbonate compounds; creatine transport aides and/or creatine precursors such as, for example, guanidinopropionic acid, glycocyamine, and/or trimethylglycine (betaine); anti-fatigue agents such as, for example, beta-alanine, PEAK ATP® adenosine 5' triphosphate and/or creatinol-O-phosphate; electrolytes such as, for example, glycerol stearate and additional sources of calcium, magnesium, potassium, and/or sodium; and excipients such as, for example, calcium silicate, malic acid, and/or citric acid.

Inulin is a soluble fiber that contains a mixture or blend of different long chain fructose polymers called fructans, which are widely found in foods such as chicory root, wild yam, artichokes, onions, garlic and agave. Oligofructose or fructooligosaccharide (FOS) is a subgroup of inulin, which contains short chain sugar molecules. Inulin and oligofructose contain the same type of fructose bonds, which cause both ingredients to be non-digestible by human intestinal enzymes. Therefore, they pass through the mouth, stomach and small intestine without being metabolized. Inulin possesses a low glycemic response and can be utilized to control the release rate and blood glucose response of the nutritional composition.

Effervescence may be accomplished with the addition of a bicarbonate compound including, but not limited to, sodium bicarbonate or potassium bicarbonate in combination with various acids such as, for example, malic acid or citric acid for the release of carbon dioxide and the creation of an acidic or low pH nutritional composition. The effervescent nutritional composition may allow for a more uniform delivery of ingredients thereby improving oral absorption.

Guanidinopropionic acid (β-GPA) [N-(Aminoiminomethyl)-beta-alanine] is a creatine analog that has been shown in animal studies to promote insulin sensitivity and fat burning. Guerrero-Ontiveros and Wallimann have demonstrated in animals that following β-GPA treatment, creatine transport activity actually increased, resulting in an increased uptake of supplemented creatine.

Guanidinoacetic acid (glycocyamine) is a guanidine compound or glycine analog that is naturally produced in the human body and is involved in the biosynthesis of creatine. Creatine, also known as alpha-methyl-guanidinoacetic acid, is simply methylated glycocyamine or guanidinoacetic acid. The oral combination of guanidinoacetic acid and trimethylglycine (creatine precursor method) is designed to form creatine phosphate in the body as first suggested in U.S. Pat. No. 2,761,807. In 1956, oral creatine monohydrate was not established as an effective means to increase intramuscular creatine phosphate. The California Research Foundation developed the creatine precursor method to increase creatine phosphate levels in certain individuals.

Trimethylglycine (betaine) is an amino acid derivative found in various plants, primarily functions as a methylating agent, and is involved in the biosynthesis of creatine. Trimethylglycine (betaine) as a stand-alone ingredient has been shown to be a powerful ergogenic aid. Research has demonstrated that oral trimethylglycine (betaine) given to weight training individuals increased bench-throw power by 16% and isometric bench-press force increased by 28% compared with placebo.

Beta-alanine is the only naturally occurring beta amino acid with unique ergogenic properties. Oral ingestion of beta-alanine increases the naturally occurring dipeptide carnosine (beta-alanyl-L-histidine) in muscle fiber. Strenuous exercise causes an accumulation of hydrogen ions and lactic acid, which causes the burning sensation in muscle fiber otherwise known as muscular fatigue. Adequate muscle carnosine buffers hydrogen ions and lactic acid accumulation. The ergogenic effect of the creatine system is inhibited by hydrogen ions and lactic acid accumulation. The combination of beta-alanine and creatine enables creatine to function beyond the creatine rate limiting system thus resulting in superior physical performance.

PEAK ATP® is an orally absorbable form of adenosine 5' triphosphate, which is a nucleotide consisting of adenosine or an adenine ring with a ribose sugar complexed with three phosphate groups. Oral administration of PEAK ATP® has been shown to elevate adenosine 5' triphosphate levels in blood and tissue, improve delivery of nutrients and oxygen, regulate vascular tone and enhance cerebral blood flow. These beneficial functions can result in improved energy, strength, recovery, muscle performance and reduced fatigue.

Creatinol-O-Phosphate is a guanidine compound or analog which contains a hydroxyl functional group unlike creatine phosphate, which contains a carboxyl functional group. Creatinol-O-Phosphate appears to donate its phosphate group for improved resynthesis of ATP or adenosine 5' triphosphate, which can provide improved strength, endurance, recovery and muscle performance.

After an extensive review of the scientific literature regarding the herein described nutritional composition and its functionality, it then became the focus of the disclosed method to develop a nutritional composition that could be administrated orally as an effective means of regulating glucose release. In addition to peroral use, several other routes such as transdermal, sublingual, intranasal, or parenteral, can be used to effectively administer this nutritional composition. Other dosage forms and applications include capsules, tablets, caplets, liquids, beverages, liquid capsules, powders, or functional food products. Nutritional compositions for use in connection with a method for promoting glycogen conservation and/or glycogen synthesis during exercise is suitably provided in an orally ingestible form such as, for example, in the form of a tablet, capsule, beverage, beverage powder mix, dietary or nutritional supplement, or consumable food item.

Solid nutritional compositions for oral administration in connection with a method for promoting glycogen conservation and/or glycogen synthesis during exercise may contain, in addition to the above enumerated nutritional composition ingredients or classes of ingredients, suitable carriers such as corn starch, gelatin, acacia, microcrystalline cellulose, kaolin, dicalcium phosphate, calcium carbonate, sodium chloride, or alginic acid. Disintegrators that can be used include, without limitation, microcrystalline cellulose and alginic acid. Tablet binders that may be used include acacia, methylcellulose, sodium carboxymethylcellulose, polyvinylpyrrolidone, hydroxypropyl methylcellulose, and ethyl cellulose. Lubricants that may be used include magnesium stearates, stearic acid, silicone fluid, talc, waxes, oils, and colloidal silica.

Liquid nutritional compositions for oral administration in connection with a method for promoting glycogen conservation and/or glycogen synthesis during exercise can be prepared in water or other aqueous vehicles. In addition to the above enumerated ingredients or classes of ingredients, the liquid nutritional compositions can contain various suspending agents such as methylcellulose, alginates, tragacanth, pectin, kelgin, carrageenan, acacia, polyvinylpyrrolidone, and polyvinyl alcohol. The liquid nutritional compositions may also include solutions, emulsions, syrups and elixirs containing together with the above enumerated ingredients or classes of ingredients, wetting agents, sweeteners, and coloring and flavoring agents. Various liquid and powder nutritional compositions can be prepared by conventional methods.

As disclosed herein, a method for promoting glycogen conservation and/or glycogen synthesis during exercise includes orally administering to an individual engaged in exercise or physical activity a nutritional composition including a carbohydrate source containing at least amylopectin and a dextran polymer to provide a steady release of glucose from the gastrointestinal tract to the blood stream. In accordance with certain embodiments, the nutritional composition can include a profiled carbohydrate source which utilizes multiple glucose polymers having differing peak absorption times to provide a sustained release of glucose for the full duration of a physical training session and/or athletic event and, optionally, into a post-exercise period. Advantageously, the carbohydrate source is administered in conjunction with one or more of: an insulin mimetic to promote steady absorption of the released glucose without creating an inhibitory insulin spike; free amino acids including essential and/or branched chain amino acids to support glycogen resynthesis; and glycerophosphate polymers to provide phosphate substrates for glycogen synthesis.

The oral daily doses can be between about 1 to about 1000 grams, suitably between about 1 to about 100 grams, or, between about 1 to about 30 grams. One daily dosing schedule can include one serving on training days. In another embodiment, multiple servings can be administered in a day if an individual engages is multiple training sessions (i.e., one dose or serving can be administered during each training session).

The nutritional composition and methods described above may be further understood in connection with the following Examples.

EXAMPLES

Example 1

In accordance with one embodiment, a serving of a nutritional composition includes the following ingredients:

Table 1

| Ingredient | Function |
|---|---|
| Amylopectin | Carbohydrate source/ |
| Inulin | glycogen replenishment |
| Isomaltulose | |
| Maltodextrin | |
| Corosolic acid | Insulin mimetic/ |
| Bis(picolinato)oxovanadium | decreases insulin to drive more |
| Bis(glycinato)oxovanadium | carbohydrates to muscle tissues |
| Cinnamon extract | |
| Trimethylglycine (betaine) | Creatine precursors/ |
| | converted to creatine in the body |
| Beta-alanine | Anti-fatigue agent |
| Isoleucine alpha amino-N-butyrate | Branched-chain essential |
| Valine alpha amino-N-butyrate | amino acids |
| Leucine alpha amino-N-butyrate | |
| Isoleucine nitrate | Branched-chain essential |
| Valine nitrate | amino acids |
| Leucine nitrate | |
| Histidine HCl | Straight-chain essential |
| Methionine HCl | amino acids |
| Phenylalanine HCl | |
| Lysine HCl | |
| Threonine HCl | |
| Glycerol stearate | * Source of electrolytes |
| Potassium glycerophosphate | (K, Mg, Na, Ca) |
| Magnesium glycerophosphate | * Hydration agent (glycerol) |
| Sodium glycerophosphate | * Source of phosphate |
| Calcium glycerophosphate | (phosphate loading) |
| Adenosine triphosphate (ATP) | Energy, endurance/ |
| | assist in creatine absorption and |
| | promote creatine bioavailability |
| Malic acid | Excipients |
| Calcium silicate | |

Example 2

Glycemic Response Post Administration of the Nutritional Composition of Example 1

Figure 1:
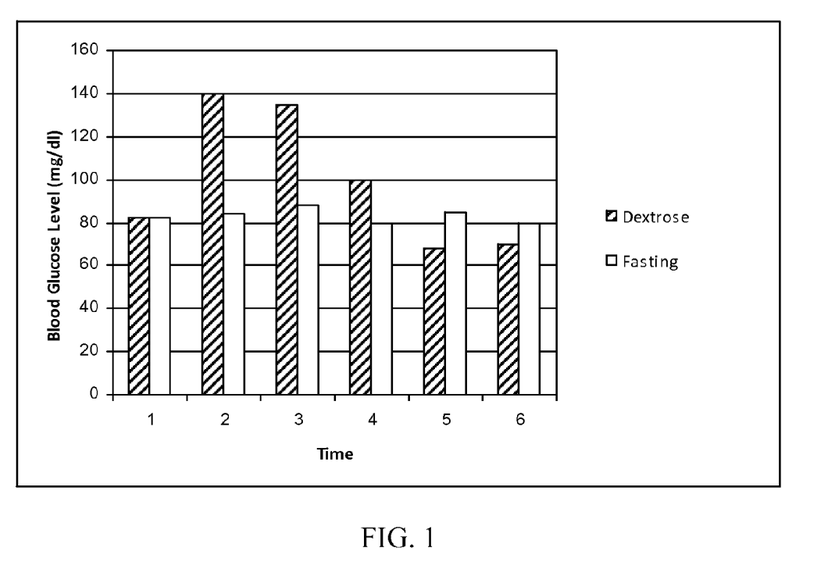
FIGS. 1 and 2 are graphical representations of the ingestion dextrose (D-glucose) compared to fasting.
Figure 2:
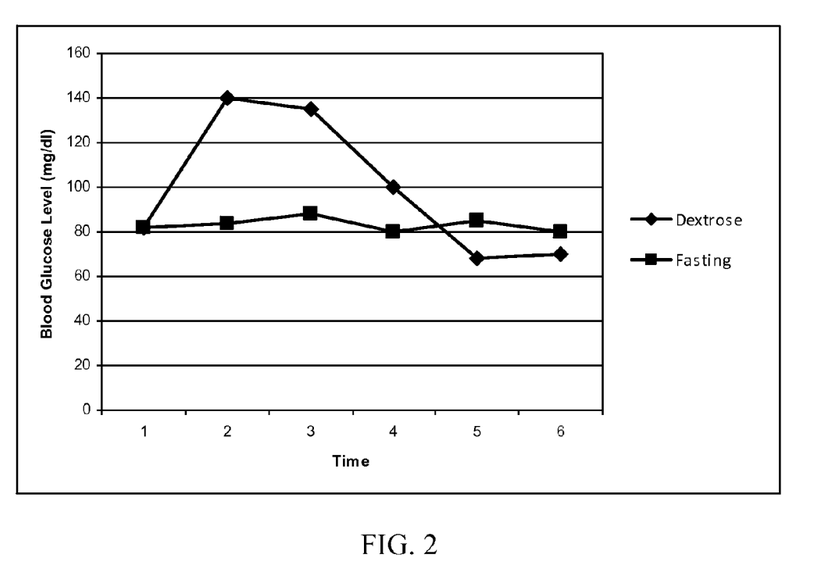
Figure 3:
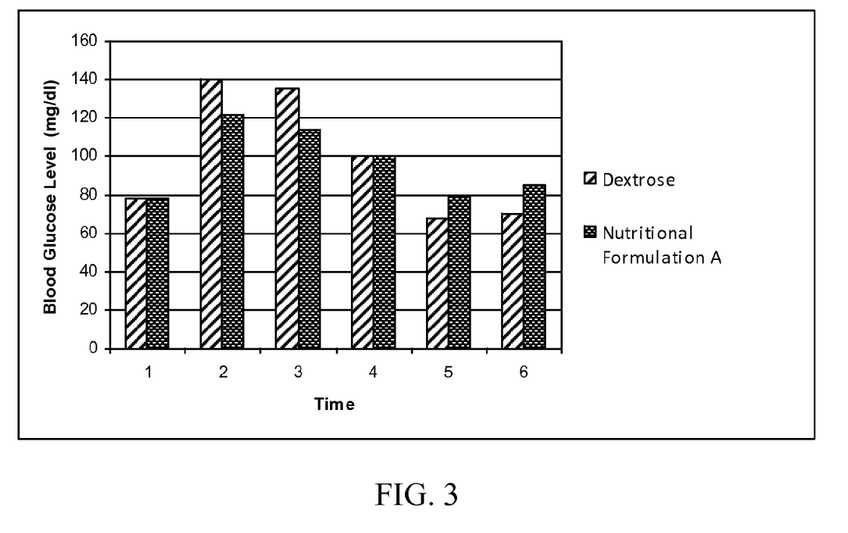
FIGS. 3 and 4 are graphical comparisons of the effects of the ingestion of a nutritional composition of the one embodiment of the invention and dextrose on blood glucose levels.
Figure 4:
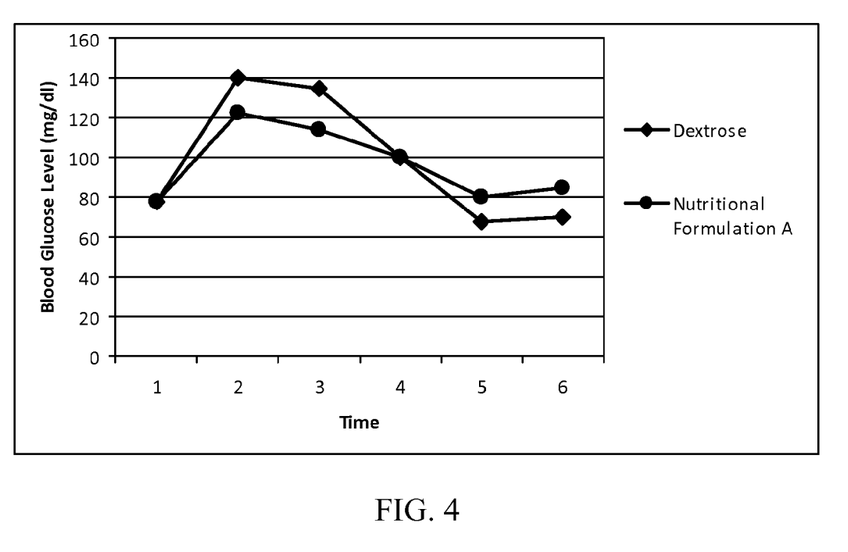
Figure 5:
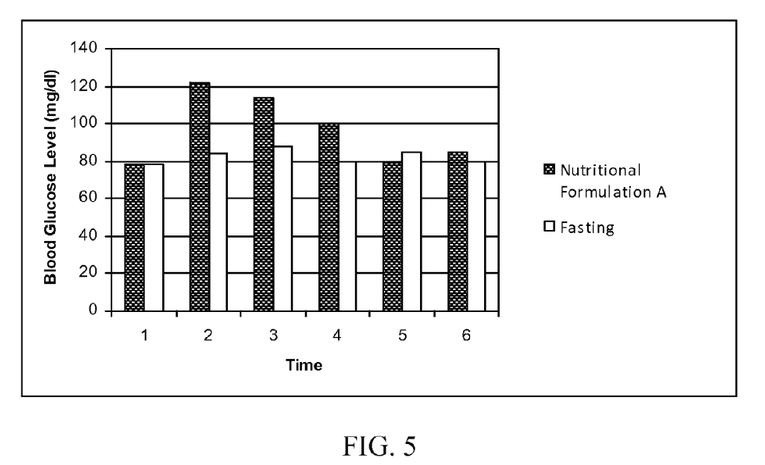
FIGS. 5 and 6 are graphical representations of the effect of the ingestion of a nutritional composition of one embodiment of the invention on blood glucose levels compared to fasting.
Figure 6:
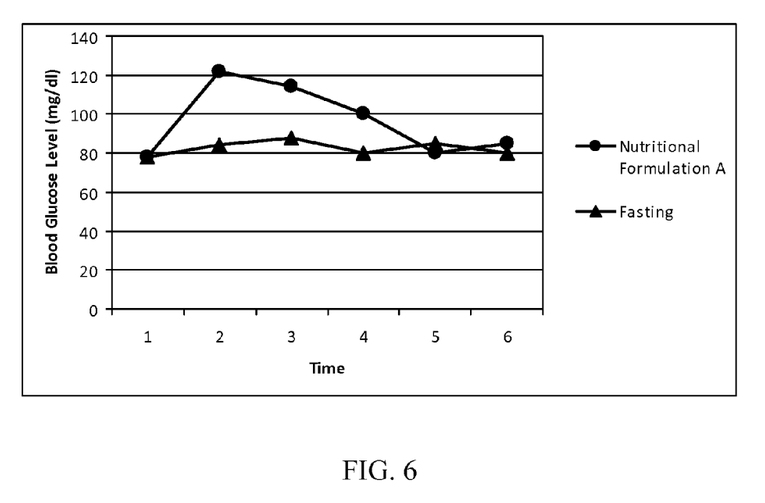

An examination of blood glucose levels was conducted in order to determine the glycemic response of the nutritional composition. One experienced weight trained male was evaluated for one day per week on the same day and time for three consecutive weeks. Fasting blood glucose was measured at rest every hour over a five-hour period in order to determine a baseline at week one. One serving of the nutritional composition described in EXAMPLE 1 was ingested and blood glucose was measured at rest every hour over a five-hour period at week two. Liquid dextrose in an amount equal in total carbohydrate to the nutrition composition was ingested and blood glucose was measured at rest every hour over a five-hour period at week three. Normal blood glucose ranges from a low of 80 mg/dl and a high of 140 mg/dl. The nutritional composition resulted in a moderate glycemic response as demonstrated by comparison with fasting and liquid dextrose blood glucose levels as shown in FIGS. 3-6.

Example 3

In accordance with another embodiment, a serving of a nutritional composition includes the following ingredients:

Table 2

| Ingredient | Function |
| --- | --- |
| Amylopectin | Carbohydrate source/ |
| Dextran | glycogen replenishment |
| Maltodextrin | Isomaltulose |
| Cinnamon extract | Insulin mimetic/ |
| Bis(picolinato)oxovanadium | decreases insulin to drive more |
| Bis(glycinato)oxovanadium | carbohydrates to muscle tissues |
| Banaba extract (18% | |
| Corosolic acid) | |
| Histidine | Straight-chain essential |
| Methionine | amino acids |
| Phenylalanine | |
| Lysine HCL | |
| Threonine | |
| Isoleucine alpha amino-N-butyrate | Branched-chain essential |
| Valine alpha amino-N-butyrate | amino acid salts |
| Leucine alpha amino-N-butyrate | |
| Isoleucine nitrate | Branched-chain essential |
| Valine nitrate | amino acid salts |
| Leucine nitrate | |
| Guanidinopropionic acid | Creatine transport |
| Glycocyamine | Creatine precursors/ |
| Trimethylglycine (betaine) | converted to creatine in the body |
| Glycerol stearate | * Source of electrolytes |
| Potassium glycerophosphate | (K, Mg, Na, Ca) |
| Magnesium glycerophosphate | * Hydration agent (glycerol) |
| Sodium glycerophosphate | * Source of phosphate |
| Calcium glycerophosphate | (phosphate loading) |
| Malic acid | Excipients |
| Calcium silicate | |

Example 4

Glycemic Response Post Administration of the Nutritional Composition of Example 3

Figure 7:
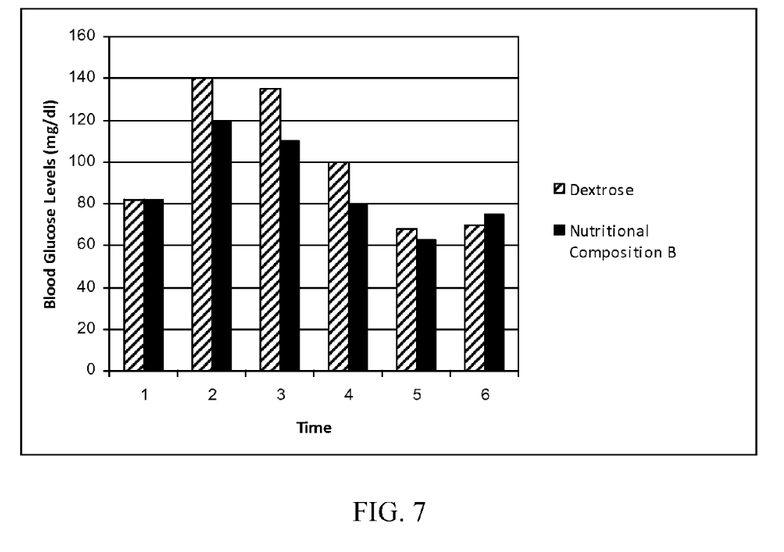
FIGS. 7 and 8 are graphical comparisons of the effects of the ingestion of a nutritional composition of the one embodiment of the invention and dextrose on blood glucose levels.
Figure 8:
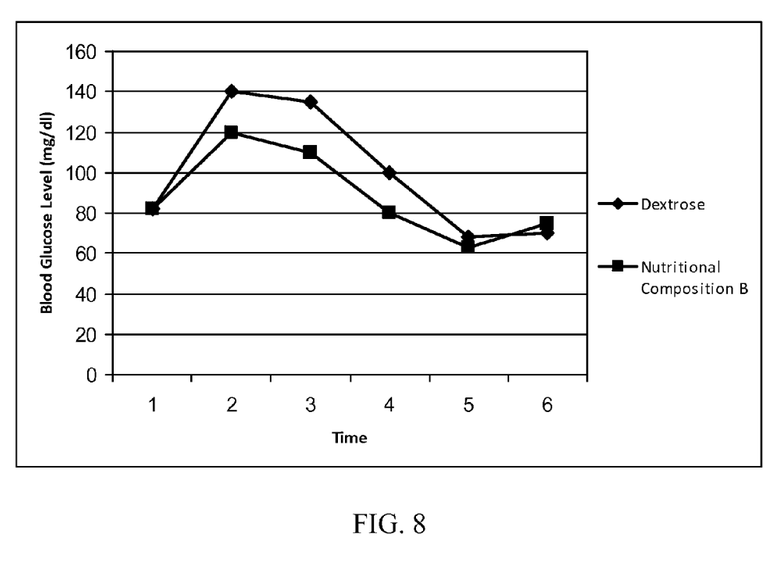
Figure 9:
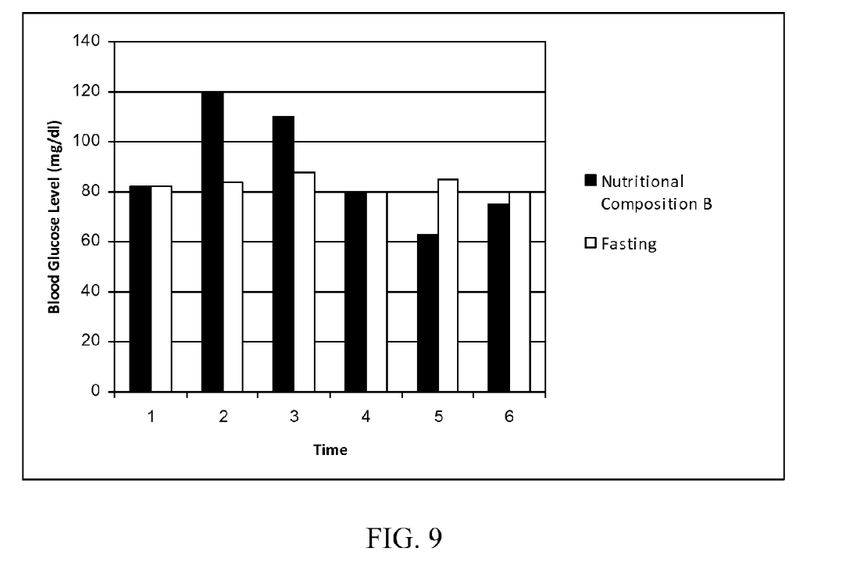
FIGS. 9 and 10 are graphical representations of the effect of the ingestion of another nutritional composition of one embodiment of the invention on blood glucose levels compared to fasting.
Figure 10:
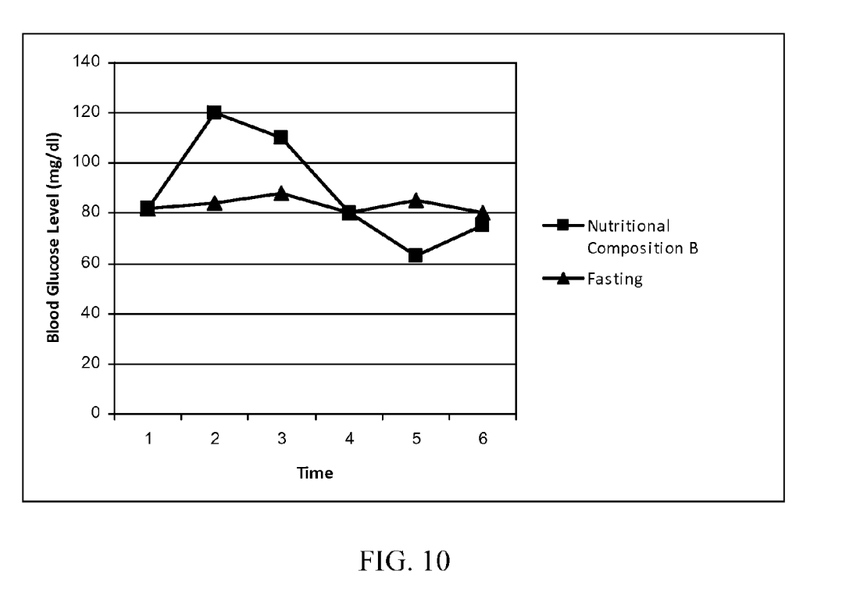

An examination of blood glucose levels was conducted in order to determine the glycemic response of the nutritional composition. One experienced weight trained male was evaluated for one day per week on the same day and time for three consecutive weeks. Fasting blood glucose was measured at rest every hour over a five-hour period in order to determine a baseline at week one. One serving of the nutritional composition described in EXAMPLE 3 was ingested and blood glucose and was measured at rest every hour over a five-hour period at week two. Liquid dextrose in an amount equal in total carbohydrate to the nutrition composition was ingested and blood glucose was measured at rest every hour over a five-hour period at week three. Normal blood glucose ranges from a low of 80 mg/dl and a high of 140 mg/dl. The nutritional composition resulted in a moderate glycemic response as demonstrated by comparison with fasting and liquid dextrose blood glucose levels as shown in FIGS. 7-10.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

We claim:

1. A method for at least one of regulating release of glucose, promoting glycogen conservation, and glycogen synthesis, comprising:
   orally administering to an individual, prior to or during exercise or physical activity, an effective amount of a nutritional composition including:
   a carbohydrate source comprising a fast absorbing carbohydrate and a slow absorbing carbohydrate; and
   an insulinomimetic compound,
   wherein a weight ratio of the carbohydrate source to the insulinomimetic compound is about 150:1 by weight.

2. The method according to claim 1, wherein the fast absorbing carbohydrate is selected from the group consisting of amylopectin, dextran, maltodextrin, and combinations thereof.

3. The method according to claim 1, wherein the slow absorbing carbohydrate is selected from the group consisting of inulin, isomaltulose, and combinations thereof.

4. The method according to claim 1, wherein the insulinomimetic compound is selected from the group consisting of an aqueous cinnamon bark extract, methylhydroxychalcone polymers, vanadium oxoanions and complexes, an extract of *Lagerstroemia speciosa*, corosolic acid, and combinations thereof.

5. The method according to claim 1, wherein the nutritional composition further comprises at least one free amino acid selected from the group consisting of histidine, methionine, phenylalanine, lysine, threonine, isoleucine, leucine, valine, salts, analogues, esters, ethers, and derivatives thereof, and combinations thereof.

6. The method according to claim 1, wherein the nutritional composition further comprises a creatine precursor, a creatine transport agent, an electrolyte, or a combination thereof.

7. The method according to claim 1, wherein a blood glucose level of the individual peaks at a lower level in comparison to an equivalent amount of dextrose.

8. The method according to claim 1, wherein a blood glucose level of the individual is at a higher level after a period of 5 hours from ingestion in comparison to an equivalent amount of dextrose.

9. The method according to claim 1, wherein a peak blood glucose level falls with a moderate blood glucose range for a human of about 90 milligrams/deciliter (mg/dl) to about 120 mg/dl.

10. The method according to claim 1, wherein a peak blood glucose level occurs later than 1 hour after ingestion of the nutritional composition.

11. The method according to claim 1, wherein the nutritional composition comprises between about 15 grams and about 45 grams of the carbohydrate source.

12. The method according to claim 1, wherein the fast absorbing carbohydrate comprises amylopectin.

13. The method according to claim 1, wherein the slow absorbing carbohydrate further comprises inulin.

14. The method according to claim 1, wherein the slow absorbing carbohydrate comprises isomaltulose.

15. A method for at least one of regulating release of glucose, promoting glycogen conservation, and glycogen synthesis, comprising:

orally administering to an individual, prior to or during exercise or physical activity, an effective amount of a nutritional composition including:
   a carbohydrate source comprising a fast absorbing carbohydrate and a slow absorbing carbohydrate, the fast and slow carbohydrates present in a ratio of 2:1 based on total weight of the carbohydrate source; and
   an insulinomimetic compound,
wherein a weight ratio of the carbohydrate source to the insulinomimetic compound is about 150:1 by weight.

16. The method according to claim 15, wherein the effective amount of the nutritional composition comprises about 15 grams to about 45 grams of a carbohydrate source including a fast absorbing carbohydrate selected from the group consisting of amylopectin, maltodextrin, dextran and combinations thereof and a slow absorbing carbohydrate selected from the group consisting of isomaltulose, inulin, and combinations thereof.

17. The method according to claim 15, wherein the insulinomimetic compound is selected from the group consisting of an aqueous cinnamon bark extract, methylhydroxychalcone polymers, an extract of *Lagerstroemia speciosa*, corosolic acid, bis-glycinato-oxovanadium (BGOV), bis-picolinato-oxovanadium (BPOV), and combinations thereof.

18. The method according to claim 15, further comprising at least one essential free amino acid and at least one free branched chain amino acid.

19. A method for at least one of regulating release of glucose, promoting glycogen conservation, and glycogen synthesis, comprising:
   orally administering to an individual, prior to or during in exercise or physical activity an effective amount of a nutritional composition including:
      a carbohydrate source comprising a fast absorbing carbohydrate and a slow absorbing carbohydrate, the fast and slow carbohydrates present in a ratio of 2:1 based on total weight of the carbohydrate source;
      an insulinomimetic compound; and
      at least one free amino acid selected from the group consisting of histidine, methionine, phenylalanine, lysine, threonine, hydrochloride salts of histidine, methionine, phenylalanine, lysine, and threonine, isoleucine, leucine, valine, nitrate salts of isoleucine, leucine, and valine, alpha amino-N-butyrate salts of isoleucine, leucine, and valine, and combinations thereof,
   wherein a weight ratio of the carbohydrate source to the insulinomimetic compound is about 150:1 by weight.

20. The method according to claim 19, wherein the fast carbohydrate is selected from the group consisting of amylopectin, maltodextrin, dextran, and combinations thereof, and the slow carbohydrate is selected from the group consisting of isomaltulose, inulin, and combinations thereof.

* * * * *